(12) United States Patent
Farjo

(10) Patent No.: US 8,058,316 B2
(45) Date of Patent: Nov. 15, 2011

(54) STAT3 INHIBITING COMPOSITIONS AND METHODS

(75) Inventor: Rafal A. Farjo, Oklahoma City, OK (US)

(73) Assignee: Charlesson, LLC, Oklahoma City, OK (US)

( * ) Notice: Subject to any disclaimer, the term of this patent is extended or adjusted under 35 U.S.C. 154(b) by 0 days.

(21) Appl. No.: 12/964,739

(22) Filed: Dec. 10, 2010

(65) Prior Publication Data

US 2011/0077306 A1   Mar. 31, 2011

Related U.S. Application Data

(62) Division of application No. 12/236,749, filed on Sep. 24, 2008, now abandoned.

(60) Provisional application No. 60/974,801, filed on Sep. 24, 2007.

(51) Int. Cl.
*A61K 31/05* (2006.01)
(52) U.S. Cl. ........................................ 514/732
(58) Field of Classification Search .................. None
See application file for complete search history.

(56) References Cited

U.S. PATENT DOCUMENTS

| | | | |
|---|---|---|---|
| 5,316,768 | A | 5/1994 | Hughes et al. |
| 7,279,469 | B2 | 10/2007 | Pierce et al. |
| 7,307,069 | B2 | 12/2007 | Karras |
| 2006/0247318 | A1 | 11/2006 | Song et al. |
| 2007/0060521 | A1 | 3/2007 | Jove et al. |

FOREIGN PATENT DOCUMENTS

WO   2006/091837 A2   8/2006

OTHER PUBLICATIONS

Hohman, T.C., Retina, (Jun. 2009), 29(6 Suppl.), S51-3(Abstract).*
Huang, et al., "Synthesis and antitumor evaluation of symmetrical 1,5-diamidoanthraquinone derivatives as compared to their disubstituted homologues.," Chem. Pharm. Bulletin, Apr. 2006, vol. 54, No. 4, pp. 458-464, the Pharmaceutical Society of Japan (Tokyo).
Johnson, et al., "Antitumor agents-CLXVII Synthesis and structure-activity correlations of the cytotoxic antraquinone 1.4-bis-(2,3-epoxypropylamino)-9,10-anthracenedione, and of related compounds." Bioorganic & Medicinal Chemistry, Aug. 1997, vol. 5, No. 8, pp. 1469-1479, Elsevier (NL).
Kaiser, P.K., Trans. Am. Ophth. Soc., (Dec. 2009), 107: 311-24 (abstract).
St. Pyrek, et al., "Naphto- and Anthraquinones of Streptomyces Thermoviolaceus WR-141. Structures and Model Syntheses," Tetrahedon, 1977, pp. 673-680, vol. 33, Issue 6, Pergamon Press Published in United Kingdom.
Teng, et al., "Design, synthesis and cytotoxic effect of hydroxy- and 3-alklylaminopropoxy-9,10-anthraquinone derivatives," Bioorganic & Medicinal Chemistry, May 16, 2005, vol. 13, No. 10, pp. 3439-3445, Elsevier (Netherlands).
Turkson, et al., "Novel peptidomimetic inhibitors of signal transducer and activator of transcription 3 dimerization and biological activity," Molecular Cancer Therapeutics, Mar. 2004;3(3):261-9, American Association for Cancer Research, Philadelphia (US).

* cited by examiner

*Primary Examiner* — Phyllis G. Spivack
(74) *Attorney, Agent, or Firm* — Scott E. Kamholz; Foley Hoag LLP

(57) ABSTRACT

A composition may include a pharmaceutical carrier and an amount, therapeutically effective for the treatment of a retinal disease, of CLT-005 (1-acetyl-5-hydroxyanthracene-9,10-dione), wherein the retinal disease is characterized by at least one of inflammation, angiogenesis, or neovascularization, and wherein the composition is prepared for administration intravitreally. The composition may be administered intravitreally to a subject's eye.

10 Claims, 16 Drawing Sheets

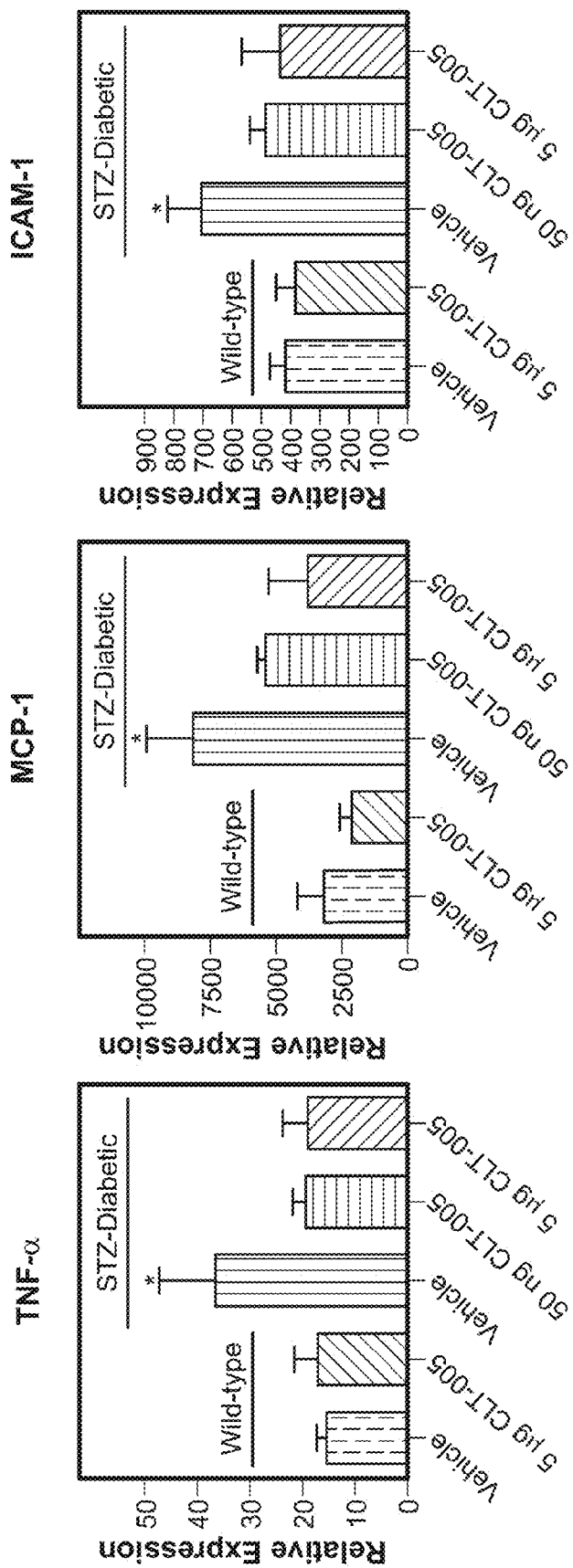

STAT3 INHIBITING COMPOSITIONS AND METHODS

CROSS-REFERENCE TO RELATED APPLICATIONS

This application is a division of U.S. application Ser. No. 12/236,749, filed Sep. 24, 2008, which claims the benefit of U.S. provisional application Ser. No. 60/974,801, filed Sep. 24, 2007 and entitled "STAT3 Inhibiting Compositions and Methods." The aforementioned applications are hereby incorporated herein by reference.

BACKGROUND

This disclosure relates to inhibition of STAT3 activity.

AMD is a rapidly growing retinal disease which primarily affects patients of age 50 years and older. Current prevalence rates in the US estimate that over 15 million US citizens are afflicted with this disorder; however, as a consequence of the rapidly growing aging population, it is predicted that the number of persons afflicted with AMD will increase 50% by 2020. Patients with AMD present with loss of their central vision that progressively worsens with age. There are two major classifications of AMD, dry and wet (or non-exudative and exudative). All patients will initially present with Dry-AMD, and approximately 85-90% of all AMD patients have the dry form of the disease. Dry-AMD features a progressive degeneration in the retinal pigment epithelial (RPE) cells, Bruch's membrane, and choroid. Another characteristic phenotypic feature is the development of subretinal deposits called drusen. These drusen have been studied with proteomics and are a compilation of numerous proteins and toxic molecules. Importantly, drusen also contain numerous inflammatory molecules that are known to initiate inflammatory cascades. Therefore, current hypotheses regarding Dry-AMD pathogenesis revolve around uncontrolled inflammation in the RPE. Since this disease primarily affects elderly patients, it is thought that years of oxidative stress lead to the initial formation of drusen, which causes the body to elicit an inflammatory response to these drusen, which then exacerbates further drusen formation. As the RPE is required to support the function of the retinal photoreceptors, this insult causes degeneration of the photoreceptors which leads to vision loss. Moreover, this inflammation leads to a breakdown of the blood retinal barrier, and formation of choroidal neovascularization (CNV) that occurs underneath the macula which is characteristic of Wet-AMD. This abnormal neovascularization causes vascular leakage of blood and fluid into the retina which leads to further visual loss in Wet-AMD patients. The progressive vascular leakage then exacerbates retinal and RPE insult and causes accelerated photoreceptor apoptosis and initiation of inflammatory pathways, which can permanently inhibit the potential for therapeutic intervention.

Several studies have demonstrated that inflammation plays a crucial role in the pathogenesis of retinal diseases and AMD. These patients have several characteristics of chronic inflammatory diseases, such as increased nitric oxide production, intracellular adhesion molecule-1 (ICAM-1) up-regulation, leukostasis and increased vascular permeability. It has been shown that the patients with proliferative retinopathies have elevated serum pro-inflammatory markers, such as TNF-α, C-reactive peptide (CRP), interleukin-1 (IL-1), IL-6, IL-18, soluble ICAM-1, and circulating vascular cell adhesion molecule-1 (VCAM-1). Induction of MCP-1, IL-8 and TNF-α is also implicated in ischemia-induced retinal NV. Recent evidence has also shown that VEGF induces ICAM-1 expression and leukostasis in the retina, suggesting that VEGF is a pro-inflammatory factor.

Several large genetic population studies have been carried out to identify susceptibility loci contributing to AMD development. These studies have identified over 30 loci demonstrating significant correlation to the risk of developing AMD, depending on the population studied. Based on these results, it is suggested that AMD is a complex disease that occurs as a result of several environmental and genetic disposition elements; however, these association studies have identified a number of inflammatory-related genes that predispose individuals to AMD. In multiple populations, mutations in the complement factor H (CFH) gene have been identified that are present in a significant number of AMD afflicted individuals. CFH is present in the bloodstream and is a inhibitor of complement activation. Thus, it has been suggested that the CFH mutations observed in AMD patients may represent an inability for these individuals to restrict inflammation in the retina as a result of vascular leakage. In addition, another large association study has implicated variants of toll-like receptor 4 (TLR4) in contributing to AMD susceptibility. TLR4 has been demonstrated to play a significant role in pro-inflammatory signaling pathways, which may also contribute to the inflammation observed in AMD pathogenesis. Another TLR family member, TLR3, has been recently implicated in Dry-AMD formation. This large genetic study demonstrated that an allele of TLR3 was associated with Dry-AMD development degeneration of RPE cells. Moreover, the authors identified a protective TLR3 allele that was associated with prevention of Dry-AMD development and progression. This protective allele reduced the ability of TLR3 to activate inflammatory pathways that eventually result in RPE cell apoptosis.

It has been shown that multiple growth factors, such as VEGF, bFGF, IGF-1, PEDF, etc. in the eye are implicated in the pathogenesis of retinal diseases and AMD. Alterations of these growth factors and their receptors in diabetes have been identified in both experimental and clinical studies. VEGF is a potent mediator of vascular permeability leading to angiogenesis and a potent mitogen with a unique specificity for endothelial cells in a variety of human pathological situations. The increased VEGF levels are responsible for the retinal vascular leakage or retinal vascular hyper-permeability, and retinal neovascularization. A number of clinical and animal studies have shown that VEGF plays a pivotal role in the development of AMD. The increased expression of retinal VEGF and its receptors correlate to high retinal vascular permeability in animal models of retinal disease with neovascularization. Inhibition of VEGF and VEGF receptors can prevent retinal NV in animal models. The causative role of VEGF in AMD pathogenesis has also been well established by many animal and clinical studies. Current pharmacological treatments for AMD are inhibitors that bind VEGF and prevent subsequent initiation of pathways leading to neovascularization. Although these compounds have has success in the clinic, they fail to address the inflammatory nature of the disease.

Leptin is an adipocyte-derived cytokine that has been linked to obesity in both humans and other animal models. Activation of the leptin receptor (Lep-R), a member of the gp130 receptor family, triggers a cascade of phosphorylation events that lead to changes in cellular gene expression. Clinical studies have demonstrated that patients with diabetic retinopathy, amongst other proliferative retinal disorders, have significantly increased levels of leptin in their vitreous humor. Leptin stimulation has been shown to exert a pro-angiogenic effect both in vitro and in vivo. Treatment of human vascular endothelial cells with leptin causes a rapid phosphorylation of the transcription factor STAT3 leading to angiogenesis.

STAT3 is a transcription factor that exerts a positive effect to promote expression of several angiogenic growth factors, such as VEGF and platelet derived growth factor, and has been shown to be constitutively active in several tumors and transformed cell types. Upon phosphorylation at tyrosine 705, STAT3 monomers dimerize and translocate to the nucleus to exert an effect on gene expression. The activated pSTAT3 is known to positively regulate VEGF through a STAT3-binding site on the VEGF promoter. Additionally, pSTAT3 also causes an upregulation of several proinflammatory molecules.

The pro-angiogenic effect of leptin stimulation is mediated by the upregulation of VEGF and can be inhibited by expression of a dominant-negative STAT3 variant. Furthermore, in the OIR mouse model, mice overexpressing leptin develop more severe retinal NV, while those deficient for leptin showed markedly suppressed retinal NV. A recent study has also demonstrated that activation of STAT3 by IL-6 stimulation can result in choroidal NV, and blockade of this pathway could inhibit NV formation. STAT3 expression is observed in both the inner nuclear layer and inner plexiform layer of the retina; however, pSTAT3 is localized exclusively in neovascular retinal vessels, which suggests an intimate involvement of pSTAT3 in the formation of retinal NV.

IL-6, an inflammatory cytokine, has also been linked to the progression of Dry-AMD to Wet-AMD. A clinical study published in 2005 enrolled patients garnering early stage characteristics of Dry-AMD. The authors quantified systemic levels of IL-6 at study enrollment and at a follow-up date approximately 4 years later. The authors demonstrated a direct correlation between increased IL-6 levels and progression from dry to Wet-AMD, potentially implicating IL-6 in AMD pathogenesis and establishing it as a biomarker for disease progression. Other studies using animal models have also demonstrated that IL-6 is directly implicated in retinal neovascularization, and prevention of IL-6 signaling could attenuate neovascularization. Specifically, the authors demonstrated that inhibition of IL-6 prevented activation of STAT3 in this model, which was the mechanism to attenuate neovascularization The role of reactive oxygen species (ROS) and oxidative stress have been well established in the development of AMD-like phenotypes in several animal models. In vascular cells, a major source of ROS arises from the activity of NADPH oxidase. NADPH oxidase is a critical mediator in the downstream development of ischemia induced VEGF expression that leads to angiogenesis. Furthermore, the inhibition of NADPH oxidase prevents early inflammatory events, such as leukostasis, the lead to breakdown of the blood retinal barrier and subsequent angiogenesis. Recently, it was demonstrated that STAT3 is responsible for promoting NADPH oxidase overexpression in the retina, and inhibition of this pathway could prevent retinal inflammation, neovascularization and breakdown of the blood retinal barrier. Another recent paper demonstrated that elevated STAT3 activation during retinal inflammation leads to the ubiquitin-proteasome dependent degradation of the master phototransduction molecule, Rhodopsin. As this protein is central to the process of phototransduction, any deficiencies in Rhodopsin levels can lead to retinal degeneration and loss of visual function.

There is currently no FDA-approved therapeutics or procedures to treat Dry-AMD. The only major clinical study of significance is the Age-Related Eye Disease Study (AREDS) that was conducted by the National Eye Institute (NEI) and concluded in 2001. The study assessed the use of orally-administered antioxidants and zinc to prevent progression of Dry-AMD. The study demonstrated that high-levels of antioxidants and zinc could reduce risk of vision loss in patients with late stages of Dry-AMD; however, the treatment had no effect on patients with early or intermediate stages of the disease, for example, patients presenting with drusen that currently have little or no vision loss. In addition, the benefit of this antioxidant/zinc regimen appears to only be effective in certain populations of affected individuals. Thus, there is still a great demand to develop Dry-AMD therapies that can prevent vision loss altogether. As demonstrated by ongoing clinical trials of experimental therapeutics, the FDA-accepted endpoint for Dry-AMD treatment is the quantification of drusen number and volume, in addition to visual acuity measurements.

SUMMARY

STAT3 inhibiting molecules and compositions prevent intraocular neovascularization. STA-21 and related compounds, including CLT-005, are shown to prevent dimerization of STAT3, thereby inhibiting STAT3 activity and inflammation. Inhibition of STAT3 prevents STAT3 from transcriptionally activating downstream gene targets that are known to be associated with retinal inflammation, neovascularization, vascular leakage, and thus such disorders as age-related macular degeneration.

DRAWINGS

The above-mentioned features and objects of the present disclosure will become more apparent with reference to the following description taken in conjunction with the accompanying drawings wherein like reference numerals denote like elements and in which:

FIG. 1 is a schematic diagram modeling the structure of dimerized STAT3 based virtual database screening;

FIGS. 2A, 2B, and 2C are schematic diagrams of modeling embodiments of small molecules that can block STAT3 dimerization based virtual database screening;

FIGS. 3A, 3B, and 3C are embodiments of graphs and immunoblot analyses demonstrating inhibition of Stat3 activity by STA-21;

FIGS. 6A, 6B-1, 6B-2, 6B-3, 6B-4, 6B-5 and 6B-6 are embodiments of experiments showing STA-21 induced apoptosis of breast cancer cells with constitutive STAT3 signaling, but not in cells lacking constitutive STAT3 signaling;

DETAILED DESCRIPTION

Figure 1:
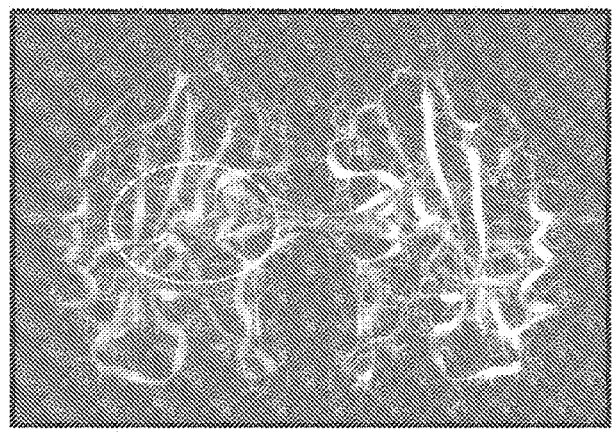

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, biological, electrical, functional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

This application incorporates by reference the following: U.S. Patent Application Publication No. US2006/0247318, filed 24 Feb. 2006; U.S. Patent Application Publication No. US2007/0060521, filed 28 Aug. 2006; and U.S. Pat. No. 7,307,069.

As used herein, the term "eye-related disease" shall mean diseases of the eye characterized by at least one of inflammation, angiogenesis, or neovascularization.

Age-related macular degeneration is expressly contemplated as falling within the definition of "eye-related disease." Other diseases include ocular disease characterized by overactive wnt pathway signaling, overexpression of LRP5 or LRP6, diabetic retinopathy, diabetic macular edema, retinitis, endophthalmitis, and uveitis.

As used herein, the term "agent" shall mean a compound that has a beneficial effect in treating a disease.

As used herein, the term "effective amount" shall mean an amount of agent administered that effects a beneficial result in treating an eye-related disease in an animal.

STAT3 is a transcription factor that is found as an inactive monomer in the cytoplasm. Upon activation of many of the Jak/gp130 family cell surface receptors, STAT3 becomes phosphorylated (pSTAT3), dimerizes, and translocates to the nucleus to exert a strong influence on gene expression. The targets of pSTAT3 include many pro-inflammatory cytokines, such as tumor necrosis factor α (TNF-α), IL-6, and IL-10, IL-12, and MCP-1. Several of the downstream targets of STAT3, including IL-6 and IL-10, are ligands for Jak/gp130 receptors and produce positive feedback to amplify the inflammatory response.

Several groups have demonstrated that these pro-inflammatory molecules are upregulated by corneal cells in response to pathogenic factors. In addition, STAT3 activation is also a key mediator of neovascularization, a process that leads to enhanced breakdown of the BRB in the adult eye. Thus, the inhibition of pSTAT3 and its activation of early response pro-inflammatory and pro-angiogenic genes represents an ideal target for preventing inflammation, neovascularization, or vascular leakage.

New anti-inflammatory and anti-neovascularization therapies are needed for the treatment of eye-related diseases, such as age-related macular degeneration and endophthalmitis. For example, the destruction of ocular cells by infiltrating inflammatory cells is the major factor contributing to visual loss in patients with endophthalmitis. In an effort to prevent this unneeded inflammatory response, ophthalmologists already employ the use of intravitreal dexamethasone in an attempt to prevent the breakdown of the BRB and subsequent inflammatory cell infiltration. Although the benefit of this treatment is highly controversial and may even cause detrimental effects to some ocular cells, physicians recognize that the need to prevent this inflammatory response outweighs the negative effects.

The inventor of the present disclosure discovered innovative, specific Signal transducer and activator of transcription protein-3 (Stat3) inhibitors for the treatment of eye-related diseases and related methods. Because pSTAT3 is an active transcription factor, it exerts a strong influence on cellular activity. STAT3, amongst other proteins, are activated as a result of stimulation with ligands, such as the pro-inflammatory cytokines IL-6 and IL-10, which bind to a gp130-family receptor. As these activation cascades may be important for other biological processes, the compositions and methods of the present disclosure specifically inhibit activity of pSTAT3 rather than upstream events such as receptor binding.

Preliminary data shows that CLT-005, a STA-21 analog, is effective in reducing the retinal expression of numerous pro-inflammatory and pro-angiogenic molecules, such as TNF-α, MCP-1, ICAM-1, and VEGF. CLT-005 and the related STA-21 analogs disclosed herein provide a novel approach to the treatment of eye-related diseases ranging from age-related macular degeneration to endophthalmitis.

CLT-005 and it related analogs disclosed herein are new, small molecules that are cell permeable and inhibit STAT3 phosphorylation at low doses. CLT-005 is particularly effective inhibitor of STAT3 phosphorylation. CLT-005 is believed to reduce ocular inflammation and vascular permeability in vivo. This compound targets a new pathway for the development of therapeutics for treating inflammatory conditions such as endophthalmitis where a need exists to inhibit the over-production of pro-inflammatory cytokines that lead to breakdown of the BRB and inflammatory cell infiltration. For example, CLT-005 may be provided as an adjunct therapy to be used with intravitreal administration of antibiotics for the management of endophthalmitis, according to embodiments. According to other embodiments, CLT-005 may be provided to patients having or wishing to prevent age-related macular degeneration or diabetic retinopathy.

Age-Related Macular Degeneration (AMD) is a severe blinding disease that affects over 30% of humans over the age of 70. Patients will initially present with a form of the disease called 'Dry-AMD,' which is characterized by the appearance of deposits (drusen) behind the retina and retinal pigment epithelial (RPE) cells. These drusen deposits are thought to form as a result of oxidative stress, and some patients will progress to a later stage of the disease, called 'Wet-AMD,' where vascular leakage and abnormal neovascularization (NV) are present. Current lines of evidence suggest that drusen causes an unnatural inflammatory response in the retina and RPE. This inflammation contributes to the breakdown of the blood-retinal barrier and vascular leakage in the retina, which leads to edema, angiogenesis, and visual loss. Retinal inflammation is known to be mediated by several pro-angiogenic cytokines, such as Interleukin-6 (IL-6), tumor necrosis factor-alpha (TNF-α), monocyte chemotactic protein-1 (MCP-1), and vascular endothelial growth factor (VEGF).

These molecules act as positive feedback to accelerate local oxidative stress, retinal vascular leakage, and angiogenesis. As the prevalence of AMD continues to grow at an alarming rate, effective therapies that can reduce conversion from Dry-AMD to Wet-AMD are highly desired. Clinical studies have shown that anti-VEGF therapies have beneficial effects on preventing further angiogenesis and vision loss in patients with Wet-AMD; however, these therapies are only useful in patients that have already lost some of their vision and have no efficacy for treating Dry-AMD.

Several lines of basic and clinical research have implicated the involvement of STAT3 in the pathogenesis of retinal disease. STAT3 is a transcription factor that exerts a positive influence on inflammation, proliferation, and angiogenesis. Activation of STAT3 occurs upon phosphorylation at tyrosine 705 (pSTAT3), causing dimerization of STAT3 monomers which can then activate transcription of pro-inflammatory and pro-angiogenic genes.

STAT3 can be activated by cytokines such as leptin and IL-6. Several studies have suggested that increased levels of leptin, an adipocyte-derived hormone, are associated with pathological retinal NV, among other forms of retinopathy. Activation of the leptin receptor (Lep-R) by leptin causes a dose-dependent increase in VEGF mRNA levels in primary retinal endothelial cells. Furthermore, in the oxygen-induced retinopathy (OIR) model which develops ischemia-induced retinal NV, over-expression of this receptor caused an elevation in retinal VEGF mRNA, while ablation of Lep-R caused a marked decrease in VEGF mRNA. The increase in VEGF levels following Lep-R activation has been specifically attributed STAT3 activation. In the OIR model, pSTAT3 is observed solely in neovascular areas of the retina.

Another study demonstrated that IL-6 mediated receptor activation of STAT3 promotes choroidal NV, which could be prevented by blockade of this pathway. An important clinical study tracked the ocular levels of IL-6 in the vitreous of patients that had Dry-AMD for over four years. It has been demonstrated that as patients progressed from Dry-AMD to Wet-AMD, there was a significant increase in systemic IL-6 present in these patients, and this increase correlated to the level of disease progression. Other studies have demonstrated that NADPH oxidase is a key mediator in the production of reactive oxygen species in the retina that leads to oxidative stress and angiogenesis. Recently, it was demonstrated that STAT3 is required to promote NADPH oxidase expression in the retina, thus inhibition of STAT3 may reduce oxidative stress in the retina and RPE that is intrinsic to Dry-AMD development.

Therefore, interference with STAT3 dimerization provides a novel method for the prevention of AMD, as well as for treatment of AMD. Because STAT3's involvement in the NADHP oxidative stress pathway, interference with STAT3 provides a method for the prevention of progression of Dry-AMD to Wet-AMD. STA-21 and STA-21-related compounds are proposed as agents that are able to interfere with STAT3 and thereby prevent AMD or AMD progression.

According to embodiments, STA-21-related compounds are included in a pharmaceutical composition together with additional active agents, carriers, vehicles, excipients, or auxiliary agents identifiable by a person skilled in the art upon reading of the present disclosure. For example, the STA-21-related compounds are compounds of Formula I:

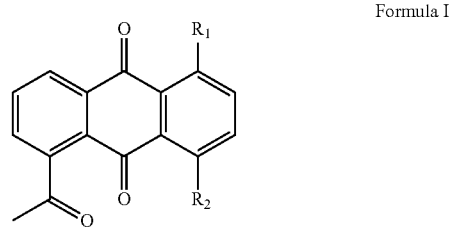

Formula I where $R_1$ and $R_2$ are independently selected from H, OH, and OMe.

According to embodiments, the STA-21-related compounds of the present disclosure are at least one of the following molecules:

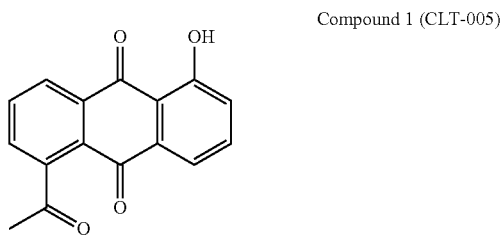

Compound 1 (CLT-005)

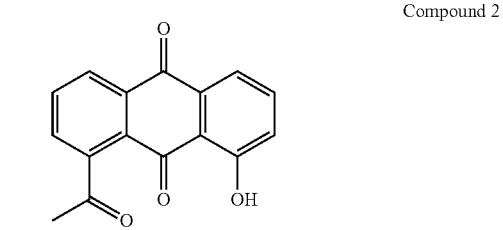

Compound 2

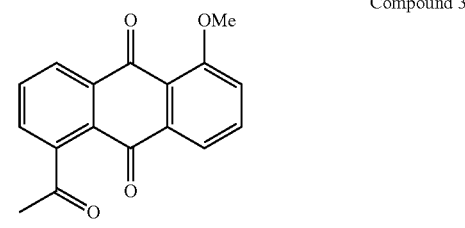

Compound 3

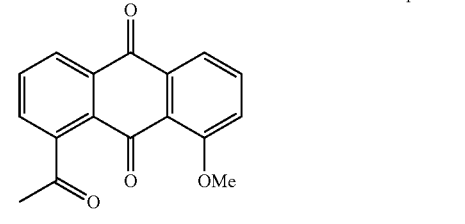

Compound 4

The pharmaceutical compositions comprise at least one pharmaceutically acceptable carrier. In such pharmaceutical compositions, the STA-21 or STA-21-related compounds form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, intravitreal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

"Subject" as used herein refers to humans and non-human primates (e.g. guerilla, macaque, marmoset), livestock animals (e.g. sheep, cow, horse, donkey, pig), companion animals (e.g. dog, cat), laboratory test animals (e.g. mouse, rabbit, rat, guinea pig, hamster), captive wild animals (e.g. fox, deer), and any other organisms who can benefit from the agents of the present disclosure. There is no limitation on the type of animal that could benefit from the presently described agents. A subject regardless of whether it is a human or non-human organism may be referred to as a patient, individual, animal, host, or recipient.

Pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL.™. (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. According to embodiments, isotonic agents, for example, sugars, polyalcohols such as manitol, sorbitol, or sodium chloride in the composition are added. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preparation are prepared by vacuum drying or freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

According to embodiments, intravitreal injection is accomplished using PLGA-based microparticles or nanoparticles (liposomes). PEG-based formulas may also be used. Accordingly, the other methods for injectable pharmaceutical compositions are expressly contemplated for intravitreal injection.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

According to embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein and according to embodiments, a therapeutically effective amount of the active compound (i.e., an effective dosage) may range from about 0.001 µg/kg to 1 g/kg body weight. The skilled artisan will appreciate that certain factors can influence the dosage and timing required to effectively treat a subject, including but not limited to the severity of the disease or disorder, previous treatments, the general health or age of the subject, and other diseases present. As such, the actual dosage may be adjusted by artisans as well known and understood by artisans.

According to another aspect, one or more kits of parts can be envisioned by the person skilled in the art, the kits of parts to perform at least one of the methods herein disclosed, the kit of parts comprising two or more compositions, the compositions comprising alone or in combination an effective amount of STA-21 or STA-21-related compounds disclosed herein according to the at least one of the above mentioned methods.

The kits possibly include also compositions comprising active agents other than the CLT-005 or related molecules disclosed herein, identifiers of a biological event, or other compounds identifiable by a person skilled upon reading of the present disclosure. The term "identifier" refers to a molecule, metabolite, or other compound, such as antibodies, DNA or RNA oligonucleotides, able to discover or determine the existence, presence, or fact of or otherwise detect a biological event under procedures identifiable by a person skilled in the art; exemplary identifiers are antibodies, exemplary procedures are western blot, nitrite assay and RT-PCR, as described in the Examples. Exemplary biological events are cytokine expression or other immunomodulating events; an exemplary active agent other than the fucose-containing glycoprotein fraction is LPS.

According to embodiments, methods are disclosed for the treatment of inflammation, angiogenesis, or neovascularization for eye-related diseases using the agents disclosed herein. According to the methods, the compounds are provided in a therapeutically effective amount to treat the eye-related disease.

According to similar disclosures, the STA-21 analogs may be provided or used to treat any disease state dependent, at least in part, on pSTAT3-dependant regulation of genes. Such disease include rheumatoid arthritis, cancer, and others.

According to other methods, the compounds of the present disclosure may be provided for or included in the manufacture of medicaments useful in treating eye-related diseases. According to still other methods, the compounds of the present disclosure may be provided for or included in the manufacture of medicaments useful in treating inflammatory diseases of all sorts, including rheumatoid arthritis, cancer, and other diseases that are influenced by the activity of pSTAT3 to activate genes in their disease pathways.

EXAMPLES

Structure-based discovery of potential STAT3-selective small molecule inhibitors.

Our approach is to use structure-based discovery to develop non-peptide and cell-permeable small molecule compounds to maximize in vivo stability and cell permeability that bind to the $SH_2$ domain of STAT3 and block the dimerization of STAT3, which in turn selectively inhibits the activity of STAT3 and inflammation. To identify potential candidate compounds that disrupt STAT3 dimerization, the crystal structure of Stat3β solved at 2.25 Å resolution on PDB entry 1BG1 was used in this study. The three-dimensional structure of STAT3β homodimer shows that the dimerization of STAT3 occurs between two $SH_2$ domains, as shown in FIG. 1. The $SH_2$ domain dimerization interface of the STAT3β (isoform of STAT3) protein is shown specifically in FIG. 1. The structure is based on PDB entry 1BG1. Two $SH_2$ domains are colored differently and the circled region indicates the target PTR binding site used in our virtual screening study.

These two $SH_2$ domains are hinged together by a loop segment (from alanine 702 to phenylalanine 716) from each monomer. The phosphoryl tyrosine 705 (pY-705) is critical for the biological function of STAT3, locates right on this loop segment and binds, together with several adjacent amino acid residues (leucine 706, threonine 708, and phenylalanine 710), to a cavity on the $SH_2$ domain of the other monomer. The targeted region defined in our virtual screening shows where the pY-705-Phe710 peptide segment binds. A small molecule that binds to this region will compete with the pY-705-containing peptide, consequently blocking the dimerization of STAT3. The chemical databases used in our virtual screening included the National Cancer Institute (NCI) database, the Merck Index, the Aldrich-Sigma catalog, and the Ryan Scientific catalog. Collectively, these four databases offered a collection of approximately 429,000 small-molecule organic compounds. With the aid of structure-based virtual screening, we narrowed down our interests from a total of 429,000 compounds to 200 top candidate compounds and were able to obtain the chemical samples for 100 compounds.

We first tested these 100 compounds using an in vitro cell luciferase assay. Of the 100 compounds tested, the most promising compound is shown on FIG. 2C which was obtained from NCI. This low molecular weight compound (STA-21) is a natural product extract, is a deoxytetrangomycin, an angucycline antibiotic with a molecular weight of 306 (FIG. 2C). The binding mode of STA-21 was predicted by the DOCK program and refined by structural optimization using the AMBER force field implemented in the Sybyl software. The refined model, shown in FIG. 2A and 2B, predicts that this inhibitor binds at the same site where the pY-705 containing peptide binds and forms a number of hydrogen bonds with nearby residues, including Arg595, Arg609, and Ile634 (FIG. 2B).

Figure 2A:
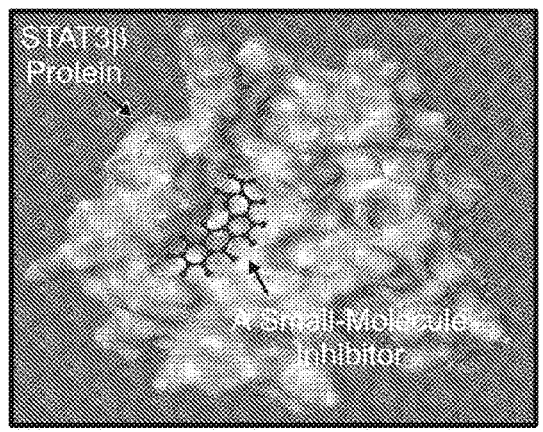
Figure 2B:
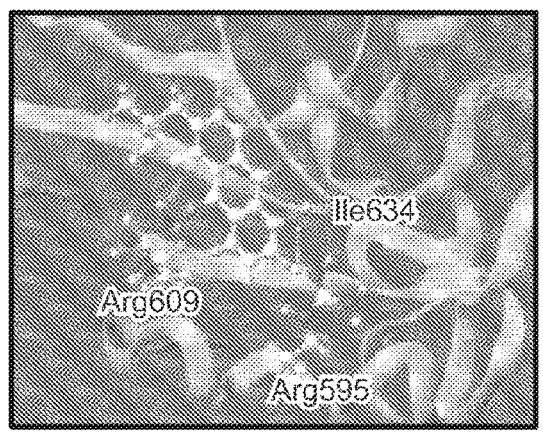
Figure 2C:
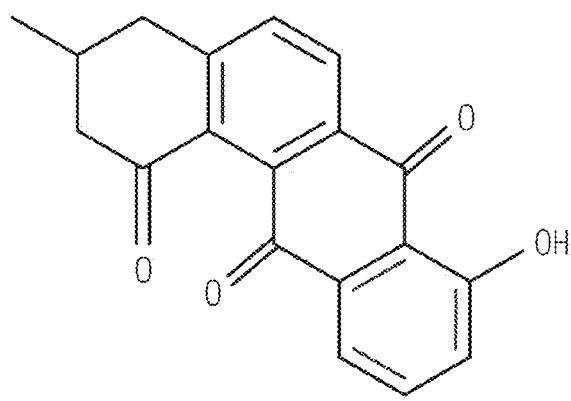

As illustrated in embodiments shown in FIG. 2A, a predicted binding model of the STA-21 to the STAT3-$SH_2$ domain. The STAT3 inhibitor is rendered by a ball-and-stick model. Molecular surface of the STAT3β $SH_2$ domain is colored with the electrostatic potentials: red for the most positively charged regions and blue for the most negatively charged regions. As illustrated by embodiments shown in FIG. 2B, specific hydrogen bonds as shown formed between the STAT3β $SH_2$ domain and the STAT3 inhibitor. The binding model was predicted by the DOCK program. Only the residues that form hydrogen bonds with STAT3 inhibitor are shown in explicit atomic models. As illustrated in embodiments shown in FIG. 2C, the chemical structure of the STAT3 inhibitor (STA-21) is shown.

2. Inhibition of STAT3-dependent Luciferase Activity.

Figure 3A:
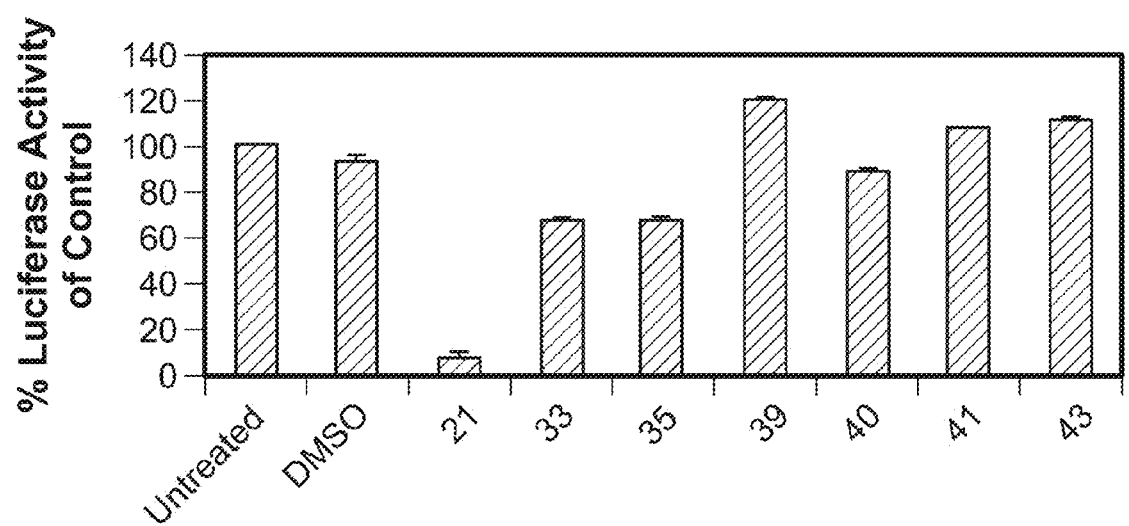
Figure 3B:
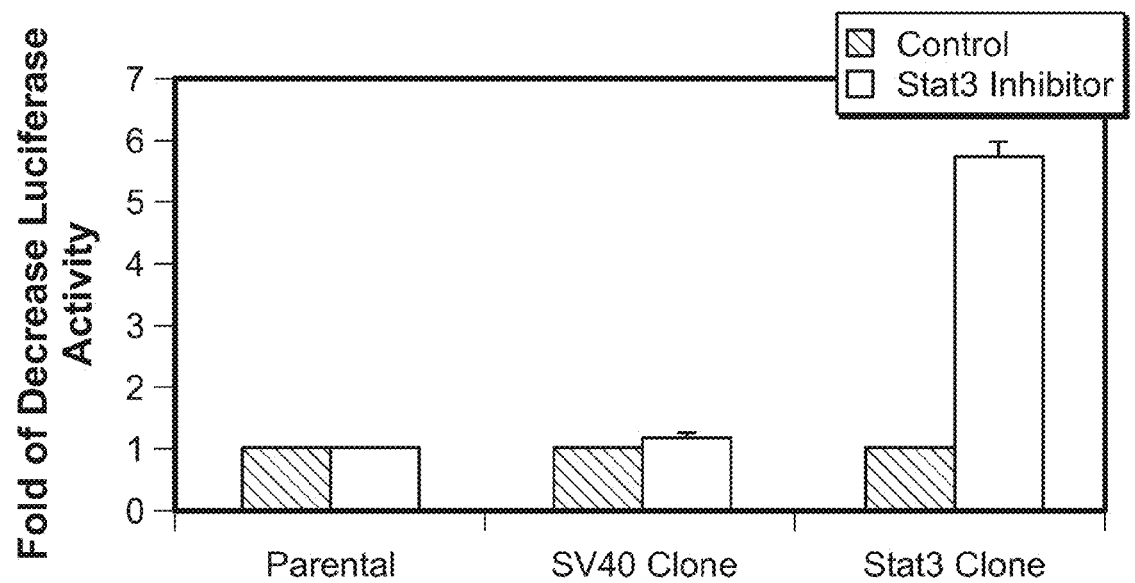
Figure 3C:
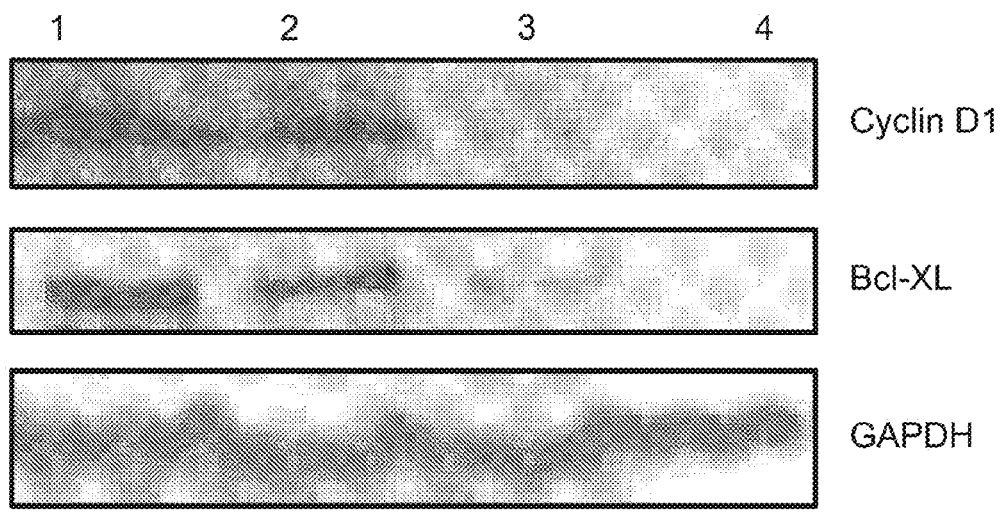

To screen the potential inhibitors that inhibit STAT3's biological activity, we established Caov-3 cancer cell line that constitutively expresses active STAT3 with a stably integrated STAT3-dependent luciferase reporter construct, pLucTKS3. This construct contains multimerized STAT3 binding sites and its activation specifically depends on STAT3. We examined the effect of eight theoretical STAT3 inhibitors to inhibit STAT3-mediated production of luciferase. One of the small molecule compounds, compound number 21 (STA-21) significantly inhibits STAT3 transcriptional luciferase activity, as illustrated in FIG. 3A, but not transcription of SV40 promoter (FIG. 3B), which is STAT3-independent. Further, this STAT3 inhibitor also inhibits the expression of two known STAT3-regulated genes, cyclin D1 and Bcl-XL (FIG. 3C). These results suggest that this compound inhibits STAT3 ability to transcriptionally induce its downstream genes.

According to embodiments of experimental data illustrated by FIG. 3A, STA-21 showed the largest reduction in STAT3-dependent luciferase expression of the potential STAT3 inhibitors. According to embodiments illustrated by FIG. 3B, the clones stably transfected with pLucTKS3 STAT3-dependent luciferase reporter or SV40 luciferase reporter were treated with 20 µM of the STAT3 inhibitor for 48h and luciferase activity was measured. DMSO (Control) had no effect on either population of cells; however, STA-21 treated cells showed a ~6-fold reduction in luciferase activity in pLucTKS3 transfected cells, but no significant difference in cells with luciferase under control of the SV40 promoter. According to embodiments illustrated by FIG. 3C, immunoblot analyses demonstrate a reduction of expression of STAT3-regulated genes, cyclin D1, and Bcl-XL by the STAT3 inhibitor, where column 1 shows untreated STAT3, column 2 is STAT3 with DMSO, column 3 is 20 µM STA-21 with STAT3; column 4 is 30 µM STA-21 with STAT3.

3. Inhibition of STAT3-DNA Binding Activity and Induction of Apoptosis by STA-21.

Figure 4:
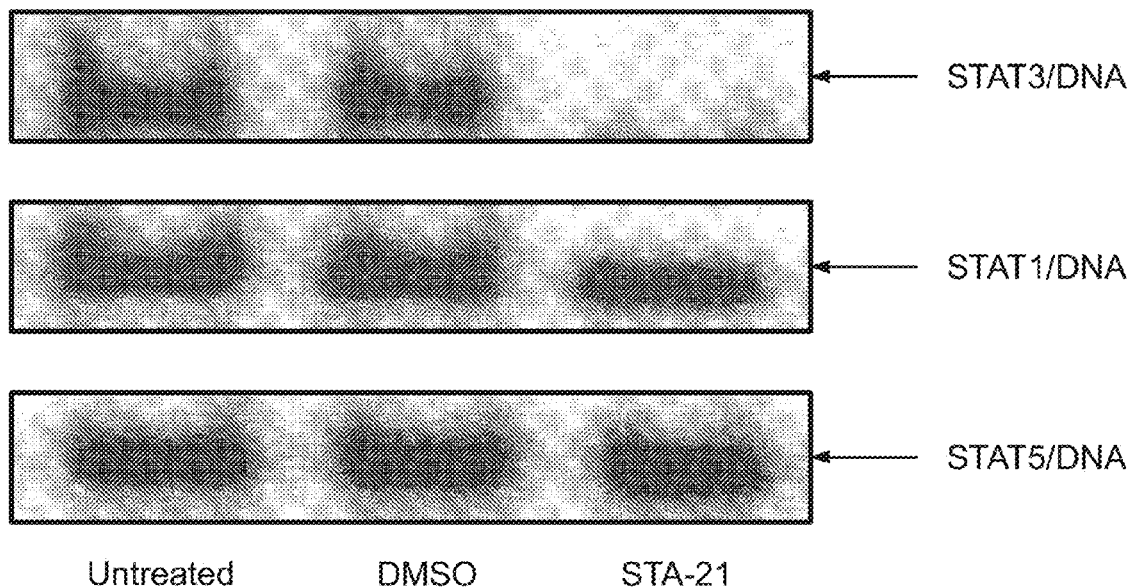
FIG. 4 is an embodiment of an electrophoretic mobility shift assay demonstrating the inhibitory effect of STA-21 on STAT3 DNA binding activity.

To further verify whether STA-21 blocks STAT3 activity, the ability of STA-21 to inhibit STAT3-specific DNA binding activity was tested using an electrophoretic mobility shift assay. MDA-MB435s cancer cells expressing constitutive active STAT3 showed strong STAT3 DNA binding activity, as shown in FIG. 4. Addition of STA-21 inhibits STAT3 but not STAT1 or STAT5 DNA binding activities (FIG. 4).

According to embodiments of experimental data illustrated by FIG. 4, MDA-MB-435s cell nuclear extract was incubated with 30 µM of the STA-21 for 30 min at room temperature, then incubated with r-32P-ATP labeled STAT3 consensus binding sequences for 20 min at room temperature. The reaction mixtures were resolved on 8% polyacylamide gel and visualized with autoradiography. STA-21 specifically blocked STAT3 DNA binding and did not inhibit DNA-binding of STAT1 or STAT5.

Figure 5A:
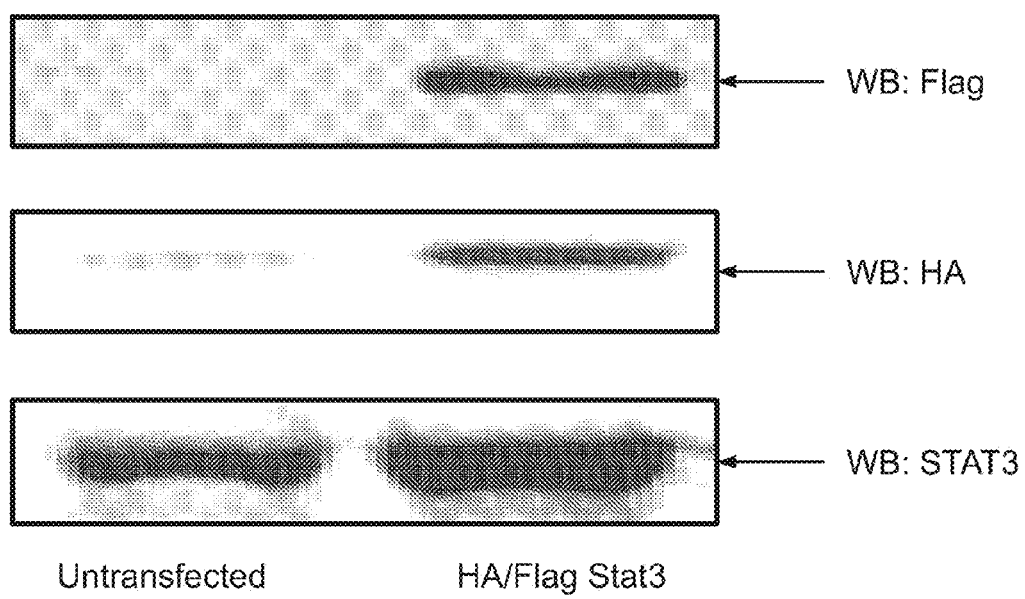
FIGS. 5A and 5B are embodiments of experiments showing the inhibitory effect of STA-21 on STAT3 dimerization.
Figure 5B:
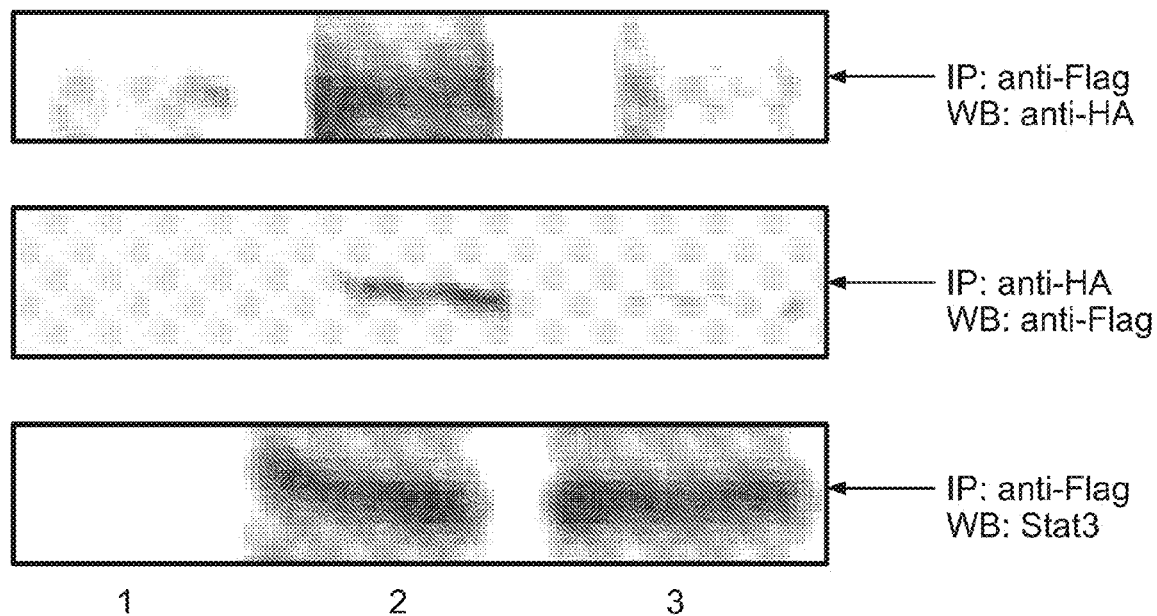

Because STAT3 dimerization is important for its biologic activity, STA-21 was further tested to see if STA-21 is able to prevent STAT3 dimerization. MDA-MB-435s cells were co-transfected with pCMV-STAT3-FLAG and pCMV-STAT3-HA plasmid constructs and immunoblot analyses were performed with anti-FLAG, anti-HA, and anti-STAT3, the results of which are shown in FIG. 5A. The cell lysates were then subjected to immunoprecipitation with an anti-FLAG or anti-HA antibody and immunoblot analyses were performed with anti-HA or anti-FLAG, respectively, the results of which are shown in FIG. 5B. The results demonstrate that both the FLAG- and HA-tagged STAT3 constructs could bind to each other (FIG. 5B, lane 2). However, cellular pre-treatment with STA-21 significantly reduced the ability of the STAT3-FLAG and STAT3-HA to dimerize.

According to embodiments of experimental results shown in FIG. 5A, MDA-MB-435s cells were transfected with pCMV-STAT3-Flag and pCMV-STAT3-HA plasmid and the cell lysate was immunoblotted with anti-Flag, anti-HA, or anti-STAT3. According to embodiments shown in FIG. 5B, MDA-MB-435s cells were co-transfected with pCMV-STAT3-Flag and pCMV-STAT3-HA plasmids and were exposed to 20 µM of inhibitor for 24h, then cell lysate was immunoprecipitated with anti-HA or anti-Flag antibody, respectively and immunoblotted with HA, Flag, or STAT3 antibody. As shown in Lane 1 of FIG. 5B, no transfection was performed. In lane 2, untreated cells were transfected with pCMV-STAT3-Flag and pCMV-STAT3-HA plasmids. In lane 3, cells were transfected with pCMV-STAT3-Flag and pCMV-STAT3-HA plasmids and treated with STA-21.

Figure 6A:
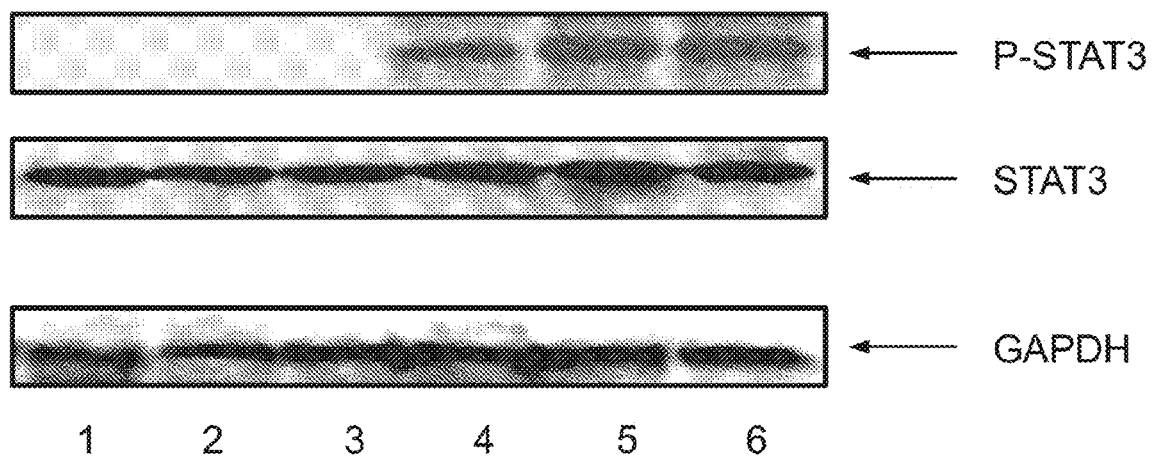
Figures 1, 6B:
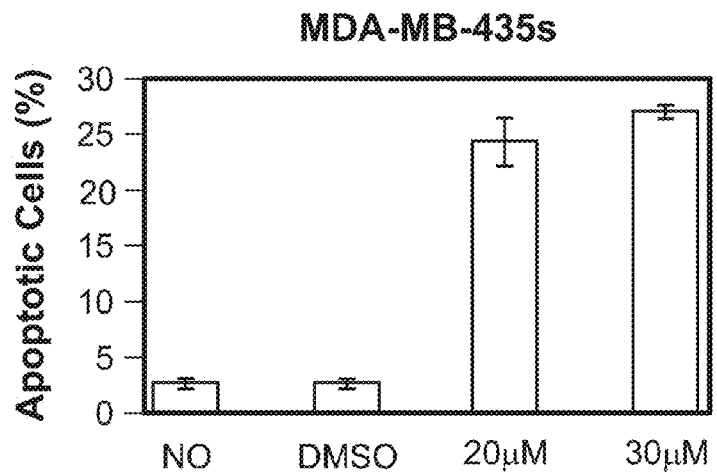
Figures 2, 6B:
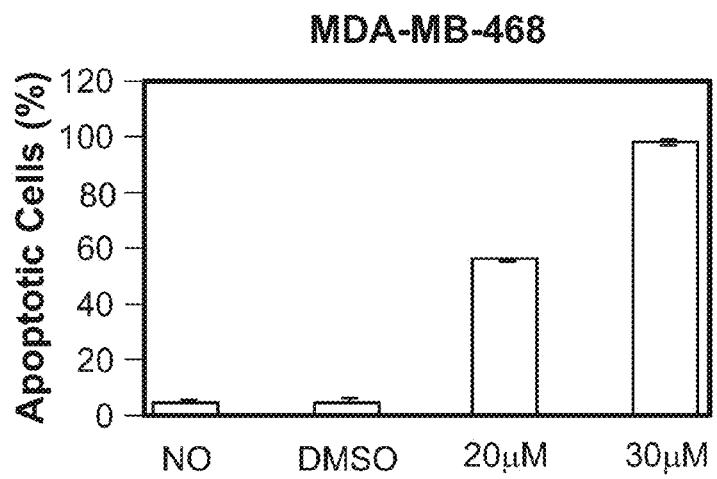
Figures 3, 6B:
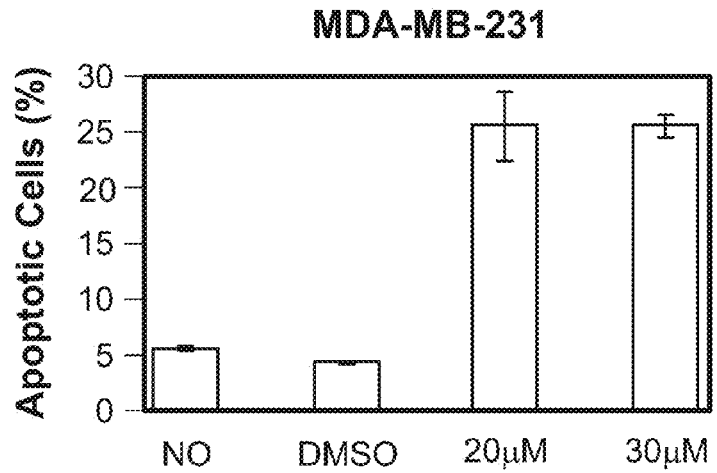
Figures 4, 6B:
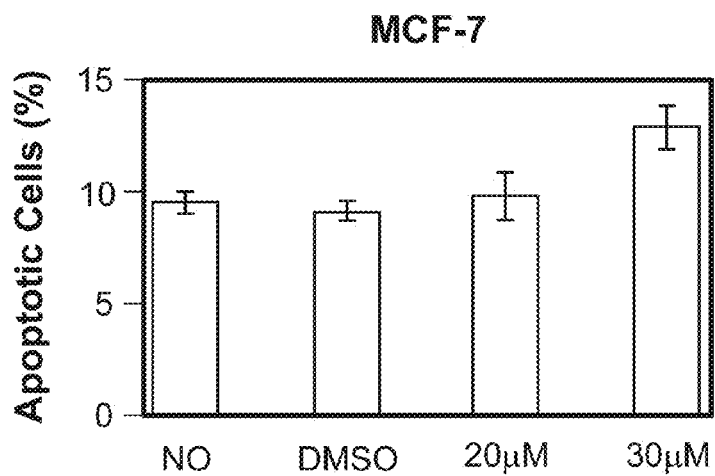
Figures 5, 6B:
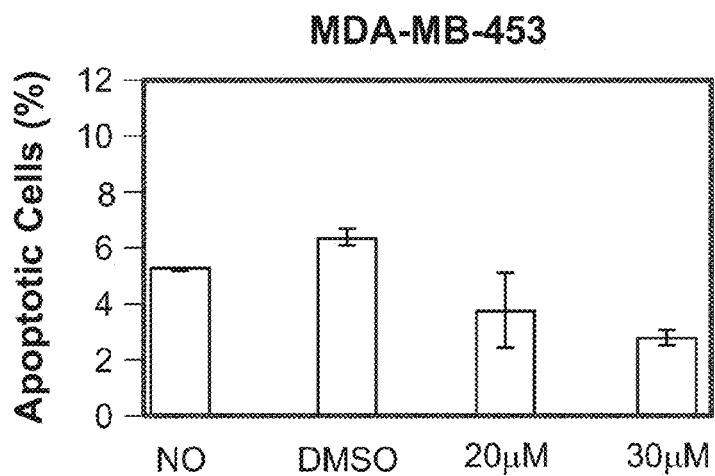
Figures 6, 6B:
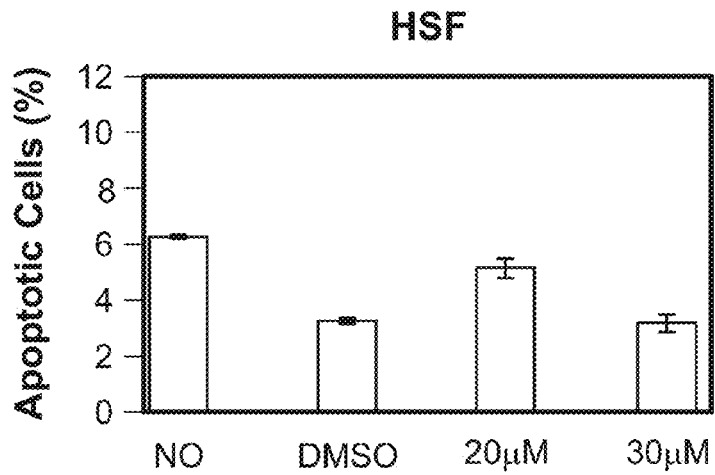

Whether STA-21 induces apoptosis selectively in breast cancer cell lines that have high levels of activated STAT3 over those that do not was also tested, the results of which shown in FIG. 6A. STA-21 selectively increased the percentage of apoptotic cells in MDA-MB-468, MDA-MB-435s, and MDA-MB-231 cell lines that express constitutively active STAT3 (5-30 fold), but had little effect in MCF-7 and MDA-MB-453 cancer cell lines and human skin fibroblasts (HSF) that lack constitutively active STAT3 (0.5-1.2 fold), as shown in FIG. 6B. It was further demonstrated that STA-21 did not inhibit phosphorylation of JAK2, Src, AKT and ERK1/2. These results suggest that STA-21 selectively targets STAT3 activity but does not inhibit STAT3 upstream regulators, Src and JAK2 and other survival or proliferation pathways such as AKT and ERK1/2. The results presented here thereby demonstrate the feasibility of our approach to identify additional STAT3 small molecule inhibitors described below.

According to embodiments of experimental data shown in FIG. 6A, the phosphorylation of STAT3 (Tyr705) in different cell lines: lane 1 with HSF, lane 2 with MCF-7, land 3 with MDA-MB-453, lane 4 with MDA-MB-231, lane 5 with MDA-MB-435s, and lane 6 with MDA-MB-468. According to embodiments shown in FIG. 6B, cell lines were treated with STAT3 inhibitor at concentrations as indicated for 48h, and apoptotic cells were detected with FACS.

4. Development of CLT-005, a Structurally Simpler Analog of STA-21

Structurally STA-21 is very rigid and it is difficult to functionalize in order to generate analogs for structure-activity-relationship studies. We sought to simplify STA-21 by retaining the anthracene moiety and the functional groups that are critical for binding to the $SH_2$ domain of STAT3 to form compound 1 (CLT-005), shown in FIG. 7.

Figure 7:
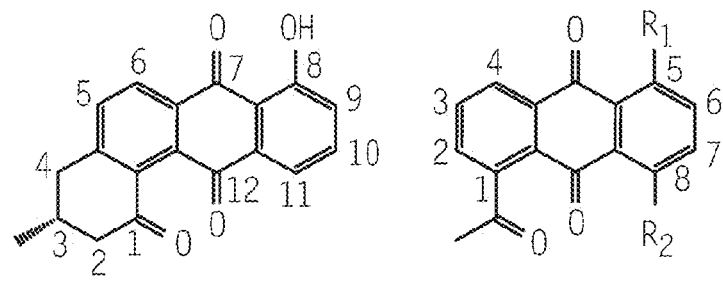
FIG. 7 are diagrams of embodiments of STA-21-related compounds.

Compounds 1-4 of FIG. 7 and STA-21 were examined for their anti-proliferative activities against three prostate cancer cell lines, DU145, PC3, and LNCaP. All three cell lines were reported to exhibit constitutive activation of STAT3 with LNCaP and DU145 cells having the lowest and highest level of expression, respectively. MCF-7 breast cancer cells, a cell line with no constitutive activation of STAT3, were used as negative control. As shown in Table 1, STA-21 exhibited good anti-proliferative activity in DU145 and PC3 and LNCaP prostate cancer cell lines with IC50 values of 12.2 and 18.7 $\mu M$ respectively. However, STA-21 did not show any antiproliferative activity in MCF-7 cells that have no constitutive STAT3 activation. The anti-proliferative activities of compound 1 (CLT-005) on DU145, PC3, and LNCaP are similar to STA-21 with IC50 values of 16.2, 13.4 and 34.1 $\mu M$ respectively (Table 1). In addition, the anti-proliferative activities are directly proportional to the level of constitutively active STAT3 expression (Table 1). Similar to STA-21, compound 1 (CLT-005) showed weak anti-proliferative activity in MCF-7 cells.

TABLE 1

The anti-proliferative activity of STA-21 and compounds 1-4 on prostate cancer cell lines DU 145, PC3, LNCaP, and breast cancer cell line MCF-7. Cells (2,000 cells/well) were treated with varying concentration of the compounds and cell associated protein was determined using MTS assay. The IC50 values represent the means of 2 experiments in triplicate. Values are the average of two separate experiments.

| Drug | DU 145 $IC_{50}$ ($\mu M$) | PC 3 $IC_{50}$ ($\mu M$) | LNCaP $IC_{50}$ ($\mu M$) | MCF-7 $IC_{50}$ ($\mu M$) |
|---|---|---|---|---|
| STA-21 | 12.2 | 18.7 | Not tested | 124 |
| Compound 1 (CLT-005) | 16.2 | 13.4 | 34.1 | 88.5 |
| Compound 2 | 31.5 | 32.4 | 31.5 | Not tested |
| Compound 3 | >100 | >100 | >100 | Not tested |
| Compound 4 | >100 | >100 | >100 | Not tested |

Figure 8:
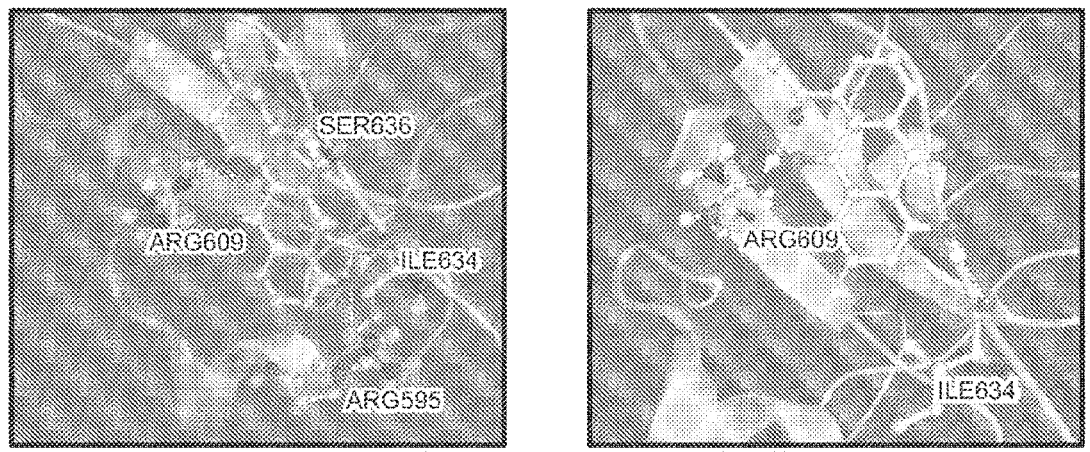
FIG. 8 are schematic diagrams of embodiments of experiments showing predicted binding models of STA-21 (A) and CLT-005 (B) to the STAT3-SH$_2$ domain.

The predicted binding model of STA-21 and CLT-005 to the STAT3-$SH_2$ binding domain is shown in FIG. 8. The molecular docking package AutoDock was used to create a model which predicts that the 8-OH group in STA-21 serves as both hydrogen bond donor (Ile 634) and acceptor (Arg 595) at the $SH_2$ domain, and the 1-keto is served as H-bonding acceptor (Arg 609). This is in agreement with the results of docking using Dock (FIG. 2B). Molecular docking reveals that CLT-005 retains the hydrogen-bonding characteristic similar to STA-21 at the $SH_2$ domain of STAT3 (FIG. 8). The models shown were computationally predicted by Autodock. Only the residues that can form hydrogen bonds with the compounds are shown.

5. CLT-005 Reduces the Retinal Levels of the Inflammatory Mediator ICAM-1 in Rats with STZ-induced Diabetes.

ICAM-1 is a key initiator of the inflammatory cascade that causes leukostasis and immune cell infiltration into a tissue. Increases in ICAM-1 have been observed in the diabetic retina, which leads to leukostasis and vascular leakage. To examine the potency of CLT-005 in reducing ICAM-1, adult rats were injected with STZ to induce diabetes. Blood glucose levels were monitored to ensure the rats entered a diabetic state. At 2-weeks post-STZ injection, rats received an intravitreal injection of 5 $\mu$l of 10 mM or 30 mM CLT-005 in one eye, and the vehicle alone in the contralateral eye. These molar doses correspond to administration of 13.3 $\mu g$ (10 mM) or 39.9 $\mu g$ (30 mM) of CLT-005 per eye. After 2 days, the retinas were dissected, placed in extraction buffer, and sonicated. Following an overnight incubation, the samples were centrifuged and the supernatant was collected to examine the levels of soluble ICAM-1. ELISA analysis demonstrated a dose-dependent decrease in ICAM-1 in retinas treated with CLT-005 as compared to controls, as illustrated in FIG. 9, demonstrating the anti-inflammatory effect of CLT-005.

Figure 9:
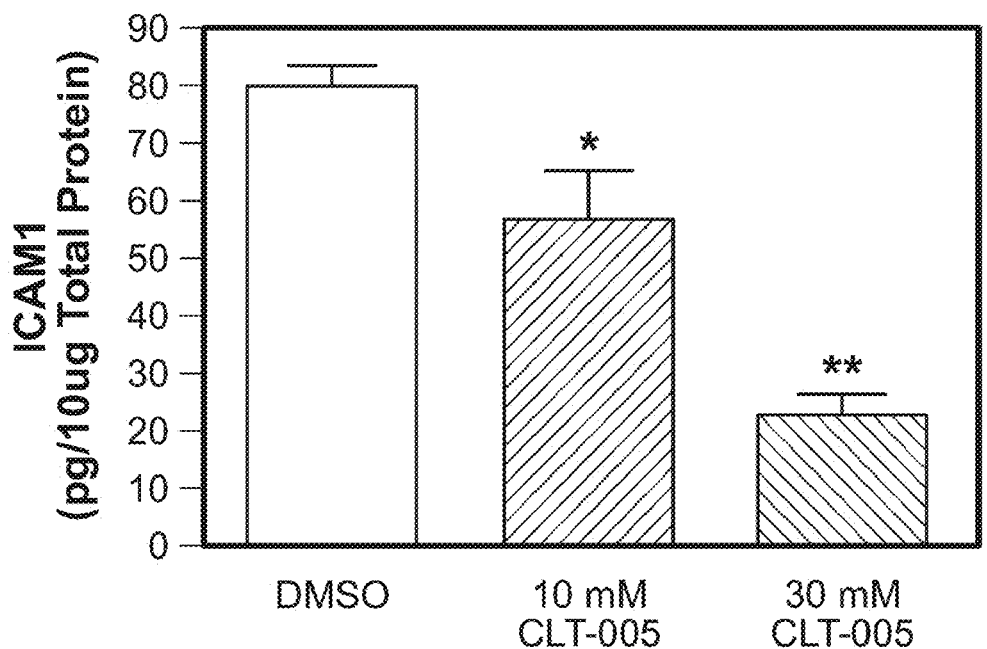
FIG. 9 is a graph of an experimental embodiment showing the reduction of retinal ICAM-1 levels in an STZ-diabetes rat model in a CLT-005 dose-dependent manner.

According to embodiments of experimental data shown in FIG. 9, two weeks following induction of diabetes with STZ, rats received an intravitreal injection of 5 $\mu L$ of 10 mM or 30 mM CLT-005 in one eye and vehicle in the contralateral eye. The retinal levels of ICAM-1 were then examined with ELISA at 2 days post-administration. A statistically significant and dose-dependent decrease of ICAM-1 levels was observed in eyes treated with CLT-005 (One-way ANOVA with Tukey's multiple comparison post-hoc test, *p<0.05, **p<0.01, n=6).

6. CLT-005 Reduces Retinal Levels of VEGF Following Intravitreal Administration in Rats with STZ-induced Diabetes.

Figure 10:
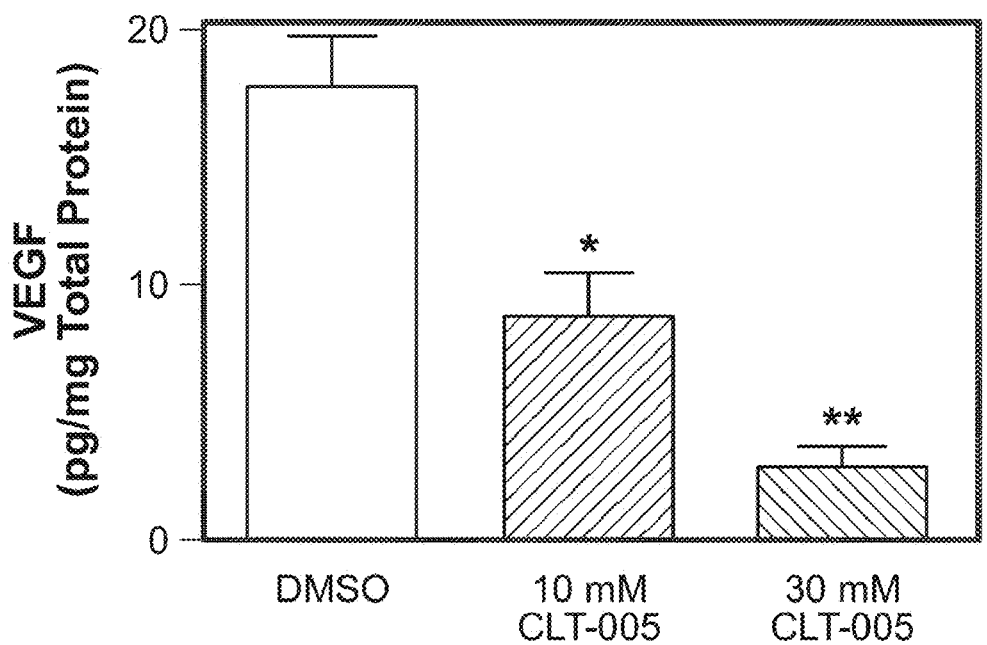
FIG. 10 is a graph of an embodiment of experimental data showing the reduction of retinal VEGF levels in an STZ-diabetes rat model in a CLT-005 dose-dependent manner.

VEGF is a potent mediator of angiogenesis and an active player in retinal neovascularization and vascular leakage. Since pSTAT3 can bind to the VEGF promoter to enhance its transcription, we sought to determine whether our STAT3 inhibitor, CLT-005, could reduce retinal expression of VEGF when administered intravitreally. To examine the potency of CLT-005 in reducing VEGF, adult rats were injected with STZ to induce diabetes. Blood glucose levels were monitored to confirm the diabetic state in the rats. At 2-weeks post-STZ injection, rats received an intravitreal injection of 5 $\mu$l of 10 mM or 30 mM CLT-005 in one eye, and the vehicle alone in the contralateral eye. These molar doses correspond to administration of 13.3 $\mu g$ (10 mM) or 39.9 $\mu g$ (30 mM) of CLT-005 per eye. After 2 days, the retinas were dissected, placed in extraction buffer, and sonicated. Following an overnight incubation, the samples were centrifuged, and the supernatant was collected to examine the levels of VEGF. ELISA analysis revealed a dose-dependent decrease in retinal VEGF levels following CLT-005 treatment, as illustrated in FIG. 10, thus establishing the efficacy of this compound in reducing factors required for ongoing retinal neovascularization.

Two weeks following induction of diabetes with STZ, rats received an intravitreal injection of 5 $\mu L$ of 10 mM or 30 mM CLT-005 in one eye and DMSO in the contralateral eye. The retinal levels of ICAM-1 were then examined with ELISA at 2 days post-administration. A statistically significant and dose-dependent decrease of VEGF was observed in eyes treated with CLT-005 (One-way ANOVA with Tukey's multiple comparison post-hoc test, *p<0.01, **p<0.001, n=6).

6. CLT-005 has Potent and Endothelial Cell-specific Antiproliferative Activity in vitro.

Figure 11:
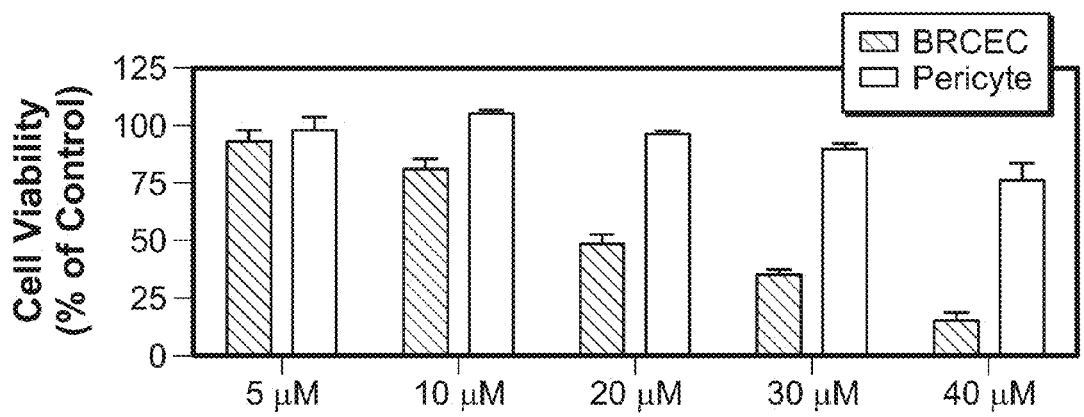
FIG. 11 is a graph of an embodiment of experimental data demonstrating anti-proliferative activity of CLT-005 in BRCEC and Pericyte cells.

According to embodiments, experiments to determine whether CLT-005 could inhibit cellular proliferation of retinal-derived endothelial cells without severely affecting pericyte cells were performed. A primary cell culture of bovine retinal endothelial cells (BRCEC) and pericytes was established. After five passages, BRCEC and pericytes were plated in 24-well plates and cultured for 24 hrs, and then treated with varying concentrations of CLT-005 and the vehicle (DMSO). After 2 days of incubation, MTT assays were performed to quantify cell viability and the dataset was normalized to viability observed in DMSO-treated cells, as illustrated in FIG. 11. The results demonstrate that in a concentration range between 20 μM and 40 μM, CLT-005 selectively inhibited proliferation of BRCECs but not pericytes.

According to embodiments, primary BRCEC and pericytes at passage 5 were plated. After 2 days of incubation with CLT-005 or vehicle, MTT assays were carried out to determine cellular viability and the data was normalized to values observed in cells treated only with DMSO. At concentrations between 20 μM and 40 μM, CLT-005 selectively inhibited BRCEC cells without severe inhibition of pericyte cells.

7. BN Rats are more Susceptible to Retinal Vascular Leakage than SD Rats in STZ-diabetic Rats.

To study the effect of diabetes on vascular permeability, the retinal vascular permeability was analyzed in diabetic rats at 1 day to 16 weeks after STZ injection and in age-matched normal controls. BN and SD rats developed similar levels of hyperglycemia after a single dose STZ injection (50 mg/kg, i.p.). However, these two strains displayed significant difference in the retinal vascular leakage of albumin.

Figure 12A:
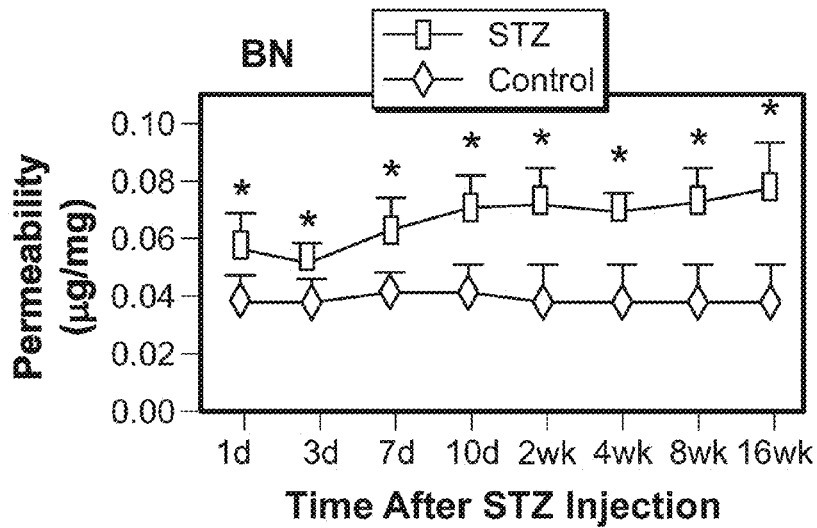
FIG. 12 is a graph of an embodiment of experimental data demonstrating the strain difference in vascular permeability in STZ-diabetic rat models.

In BN rats, the leakage occurred 1 day after the STZ injection (1.4-fold; P=0.0292) and reached a plateau at 2 wks (1.8-fold, P=0.0074). The leakage lasted for at least 16 wks after the induction of diabetes, as shown in FIG. 12A.

Figure 12B:
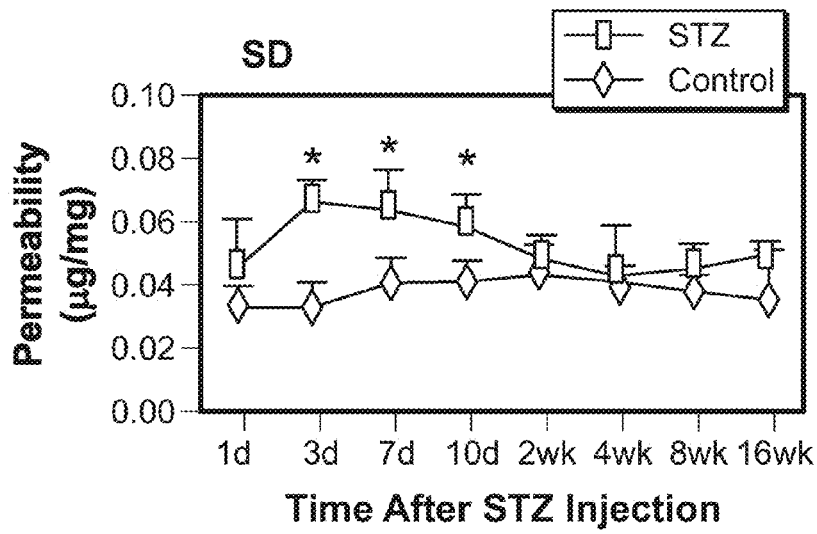

In STZ-SD rats, the leakage started at 3 days after the STZ-injection (1.3-fold; P=0.0271), reached its peak at 1 wk (1.5-fold; P=0.004) and declined to the control level by 2 wks, as shown in FIG. 12B. These results demonstrate that vascular leakage is more severe and lasts longer in BN than in SD rats at the similar hyperglycemia levels.

Retinal permeability was measured using Evans blue-albumin leakage method at different time points as indicated. Permeability was normalized by total protein concentrations in the retina and expressed as g of Evans blue per mg of proteins (mean±SD, n=4). Values significantly higher than the age-matched normal control were indicated by *(P<0.05).

8. CLT-005 Reduces the mRNA Expression of Several Pro-inflammatory and Pro-angiogenic Molecules in Rats with STZ-induced Diabetes.

Since pSTAT3 exerts a positive influence on angiogenesis and inflammation by increasing the mRNA transcription of target genes, treatment with CLT-005 was tested to identify whether CLT-005 could prevent the upregulation of these pathogenic molecules. According to embodiments, adult rats were injected with STZ to induce diabetes. Blood glucose levels were monitored to confirm the diabetic state in the rats. At 2-weeks post-STZ injection, rats received an intravitreal injection of 50 ng or 5 μg of CLT-005 in one eye, and the vehicle (DMSO) alone in the contralateral eye. To establish a baseline level of expression, non-diabetic rats of the same age also received and intravitreal injection of 5 μg of CLT-005 in one eye and the vehicle (DMSO) alone in the contralateral eye. At 24 hrs post-administration, the retinas were dissected and quantitative RT-PCR (qRT-PCR) was used to quantify the mRNA expression levels of proinflammatory molecules: TNF-α, MCP-1, ICAM-1, and IL-6; pro-angiogenic molecules: LRP-5 and LRP-6; and pro-proliferative molecules TGFB1, BCL-2, and CCND1 (FIG. 13).

This quantification revealed that in non-diabetic rats, the expression of all genes examined were largely unaffected by treatment with 5 μg of CLT-005. Following induction of diabetes, the expression of each of these molecules was increased in the retinas of STZ-diabetic rats; however, treatment with CLT-005 significantly reduced expression levels back to the baseline observed in the non-diabetic rat retina. Both the 50 ng and 5 μg doses of CLT-005 equally reduced the expression of these inflammatory molecules, demonstrating the potency of CLT-005. The expression of the pro-angiogenic and pro-proliferative molecules LRP-5, LRP-6, TGFB1, BCL-2, and CCND1 also displayed a similar expression profile. In non-diabetic rats, expression of IL-6, LRP-5, and LRP-6 were minimal, but dramatically increased following induction of diabetes. Remarkably, treatment with either dose of CLT-005 completely reduced expression of LRP-5 and LRP-6 to baseline levels. These data suggest a potential mechanism for the inhibition of retinal inflammation and neovascularization upon treatment with CLT-005.

Figures 13D, 13E, 13F:
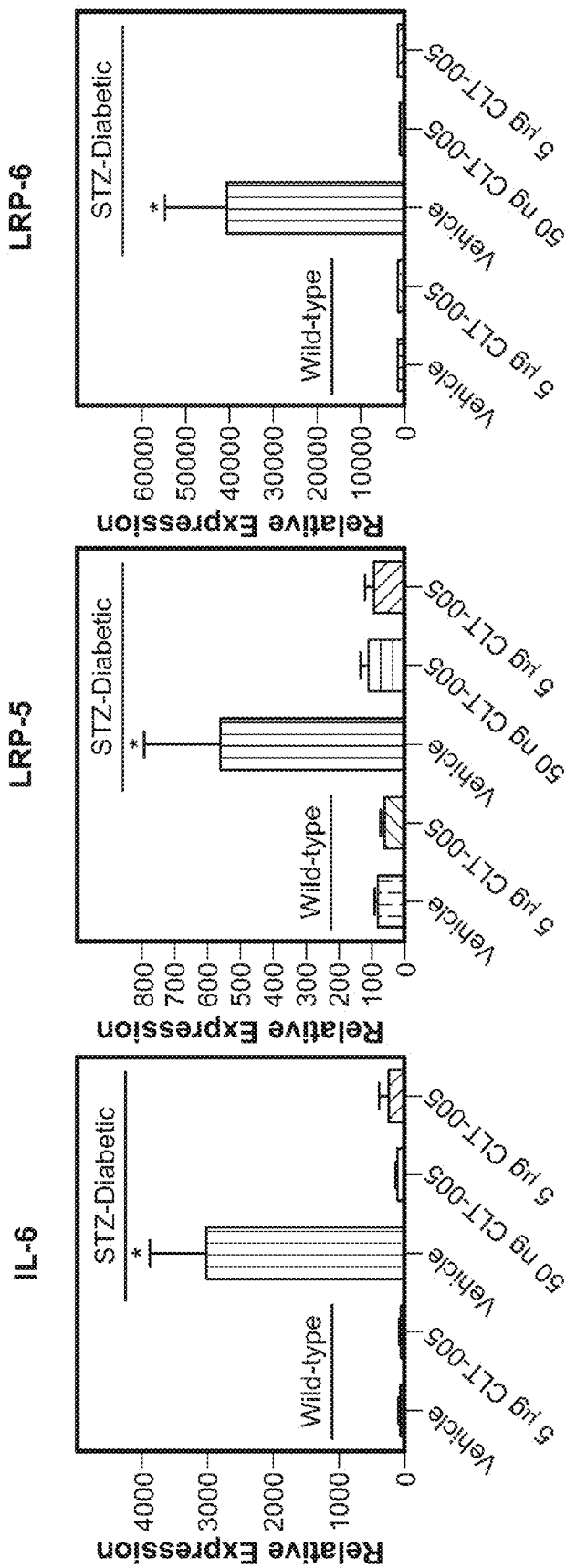
FIG. 13 are graphs of embodiments of experimental data demonstrating that CLT-005 reduces the mRNA expression of pro-inflammatory and pro-angiogenic genes following intravitreal delivery.
Figures 13G, 13H, 13I:
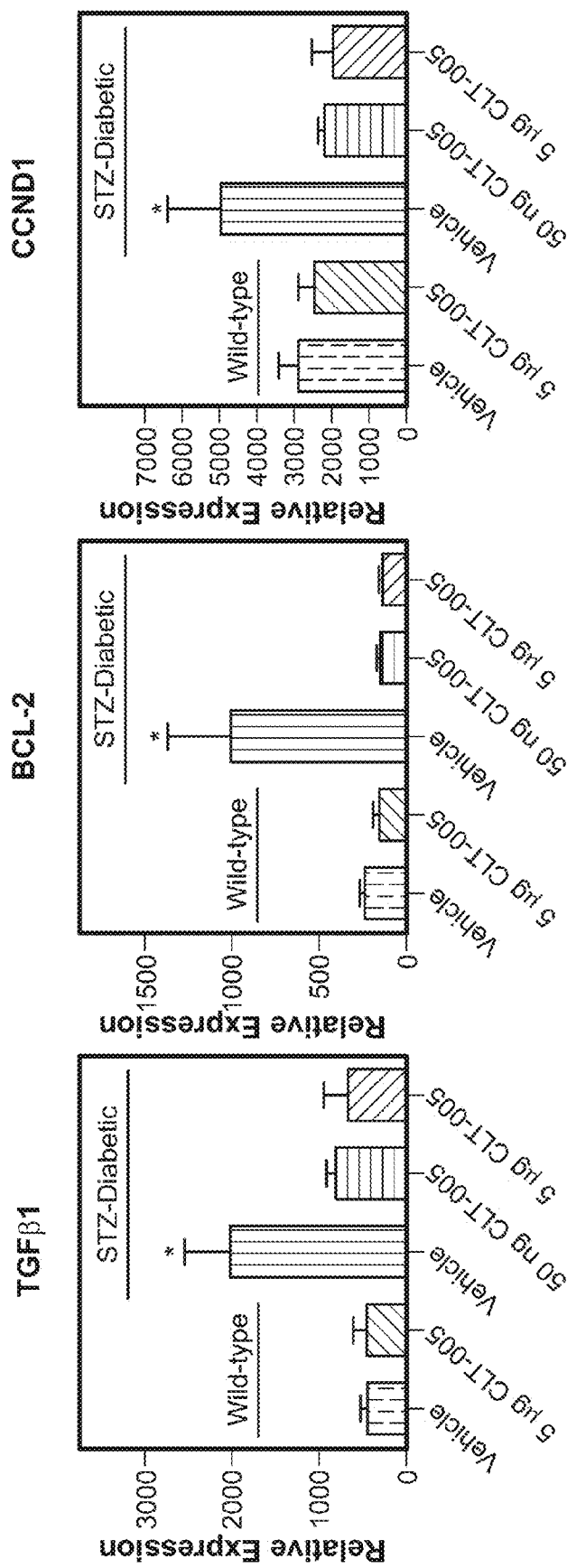

According to embodiments of experimental data shown in FIG. 13, two weeks following induction of diabetes with STZ, rats received an intravitreal injection of 50 ng or 5 μg of CLT-005 in one eye, and the vehicle (DMSO) alone in the contralateral eye. As a control, non-diabetic rats of the same age also received and intravitreal injection of 5 μg of CLT-005 in one eye and the vehicle (DMSO) alone in the contralateral eye. For all genes examined, diabetes induced expression of these genes, which was restored to baseline levels upon treatment with CLT-005. (One-way ANOVA with Tukey's multiple comparison post-hoc test, *p<0.05.)

9. CLT-005 Reduces the Retinal Vascular Permeability in Rats with STZ-induced Diabetes.

As increased retinal vascular permeability is a hallmark indicator for edema and pre-angiogenic events, we examined the effect of CLT-005 on reducing retinal vascular permeability in adult rats induced to a diabetic state by intraperitoneal injection of STZ. Blood glucose levels were monitored to confirm the diabetic state in the rats. At 2-weeks post-STZ injection, rats received an intravitreal injection of 1 μg or 5 μg of CLT-005 in one eye, and the vehicle (DMSO) alone in the contralateral eye. After 2 days, retinal vascular permeability was quantified by measuring Evans blue-albumin leakage from blood vessels into the retina. The rats were anesthetized and Evans-blue dye (30 mg/kg body weight) was injected through the femoral vein under microscopic inspection. After injection, the rats were kept on a warm pad for 3 h to ensure the complete circulation of Evans blue dye. Then the chest cavity was opened, and blood was collected through the right atrium. Rats were then perfused via the left ventricle with 1× PBS (pH 7.4), which was pre-warmed to 37° C. to prevent vasoconstriction. Immediately after perfusion, the eyes were enucleated, and the retinas are carefully dissected under an operating microscope. The Evans blue dye is extracted in formamide and by sonication and centrifugation. The Evans blue dye is then quantified by absorbance measurement at 420 nm and normalized to the total amount of retinal protein present in the harvested samples. These results demonstrated that both 1ug and 5ug of CLT-005 reduced retinal vascular permeability by nearly 50% (FIG. 14).

Figure 14A:
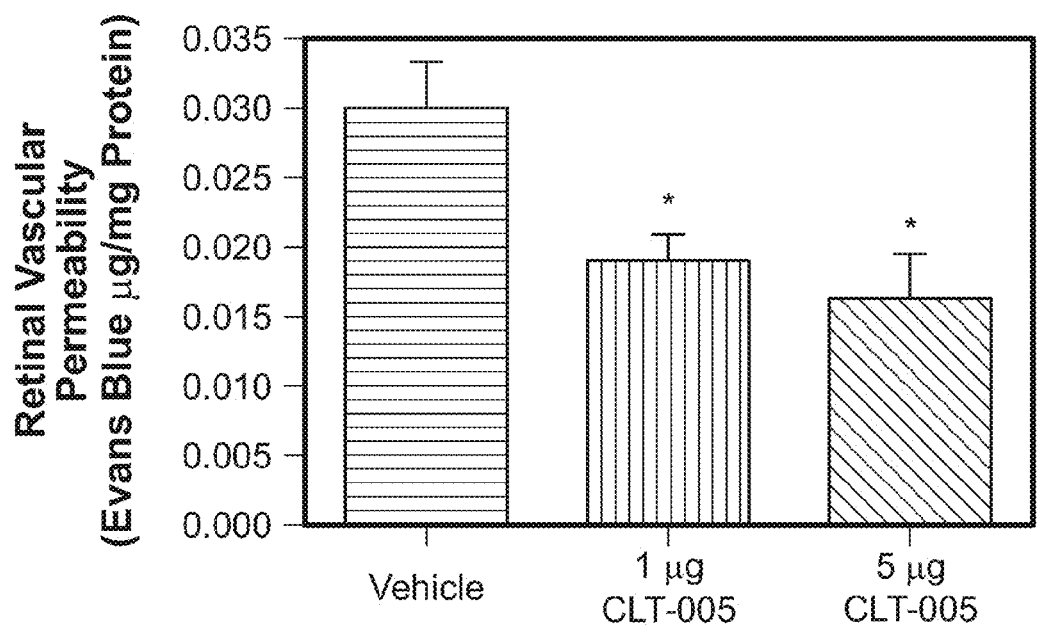
FIG. 14 are graphs of embodiments of experimental data demonstrating CLT-005 reduces retinal vascular permeability in STZ-diabetic rats.
Figure 14B:
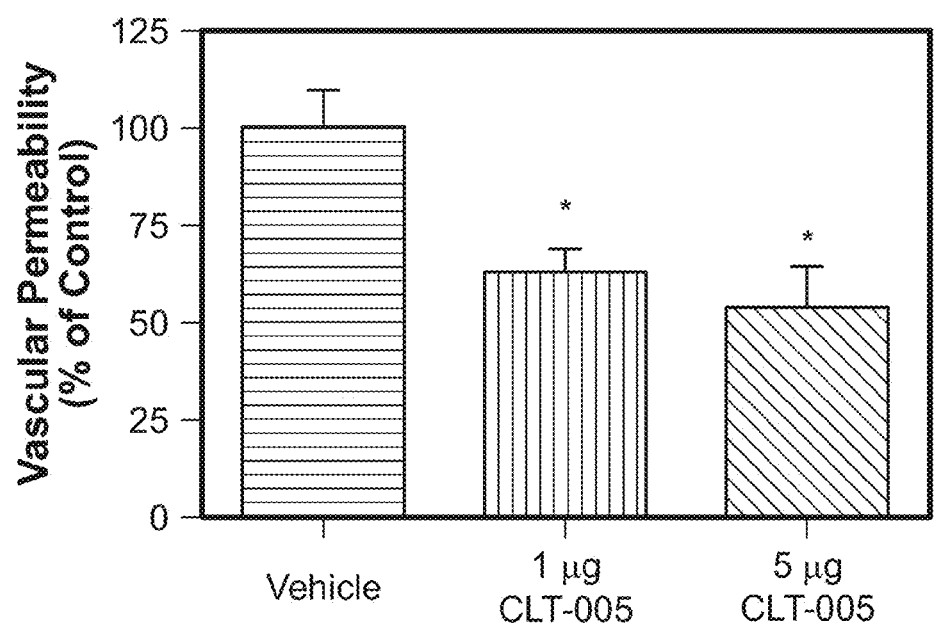

According to embodiments of experimental data shown in FIG. 14, two days following intravitreal administration of 1 μg or 5 μg CLT-005 to STZ-diabetic rats, retinal vascular permeability was quantified using the Evans Blue extravasation method. The data demonstrate that both 1 μg and 5 μg of CLT-005 reduce retinal vascular permeability in the diabetic retina. (One-way ANOVA with Tukey's multiple comparison post-hoc test, *p<0.05.)

10. CLT-005 has no Effect on Electroretinogram Responses.

Figures 15A, 15B, 15C:
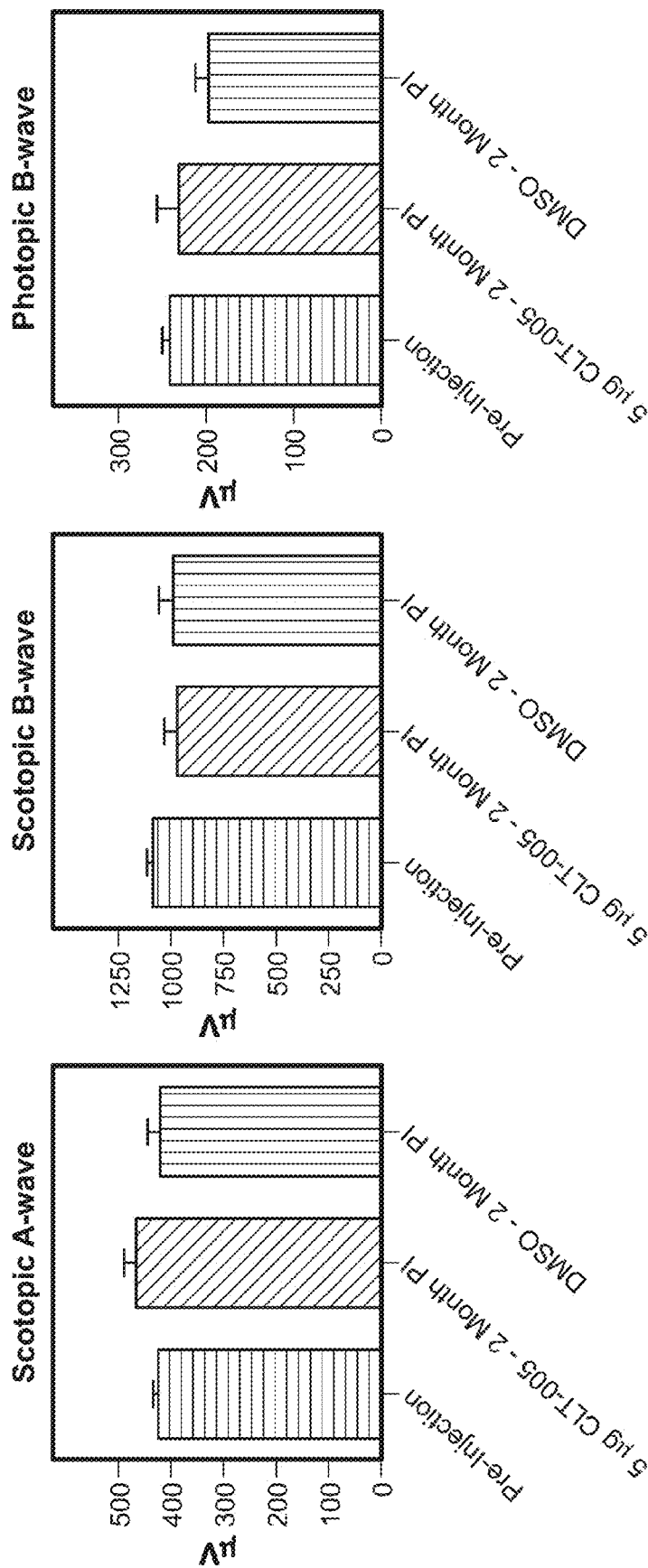
FIG. 15 are graphs of embodiments of experimental data demonstrating CLT-005 has no effect on scotopic a-wave, scotopic b-wave, or photopic b-wave amplitudes following ERG analyses.

To examine the effect of CLT-005 on visual physiology, electroretinography (ERG) on eight wild-type brown norway rats was performed. Animals were subjected to both scotopic and photopic ERG to examine the function of rod and cone photoreceptors, respectively. After acquisition of these baseline levels, all rats received an intravitreal injection of 5 μg CLT-005 in one eye, and an equal volume of the vehicle (5 μl DMSO) in the contralateral eye. At 2 months post-injection, ERG was performed and the scotopic a-wave and b-wave in addition to the photopic b-wave were quantified and compared to the baseline levels acquired before intravitreal injection (FIG. 15). The data demonstrate that intravitreal administration of CLT-005 had no effect on ERG responses and does not appear to alter visual physiology.

11. CLT-005 Formulated into Nanoparticles Reduce Expression of the Pro-inflammatory Protein MCP-1, in Rats with STZ-induced Diabetes.

Figure 16:
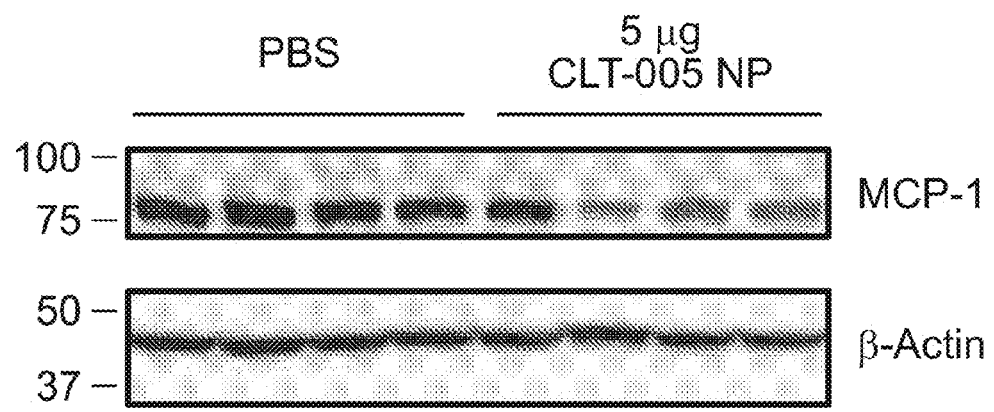
FIG. 16 are immunoblot analysis of embodiments of experimental data demonstrating that CLT-005 reduces retinal MCP-1 levels in an STZ-diabetes model.

MCP-1 is a potent cytokine that promotes the attraction of inflammatory cells into a tissue. Upon binding of MCP-1 to the chemokines receptors CCR2 and CCR4, and signals are generated to attract monocytes and other immune cells to a site of inflammation. To examine the potency of CLT-005 on reducing MCP-1 levels, we prepared sustained release nanoparticles (NPs) to package CLT-005 and performed intravitreal injections in STZ-diabetic rats. For all animals, one eye was injected with 5 μg of CLT-005 NPs and the contralateral eye received PBS as a control. At seven days post-injection, the retinas were harvested, and immunoblot analyses were performed to visualize MCP-1 levels (FIG. 16). Intravitreal delivery of CLT-005 NPs produced decreased expression of MCP-1 in three out of the four animals tested, demonstrating the anti-inflammatory efficacy of CLT-005.

According to embodiments of experimental data shown in FIG. 16, two weeks following induction of diabetes with STZ, rats received an intravitreal injection of 5 μg of CLT-005 NPs in one eye and PBS in the contralateral eye. At seven days post injection The retinal levels of MCP-1 and β-Actin were then examined with immunoblot analyses. As compared to the contralateral control eye, CLT-005 NPs reduced the expression of MCP-1 in three out of four animals examined.

12. CLT-005 Formulated Nanoparticles Produce a Sustained Reduction in the Protein Expression of VEGF.

Figure 17:
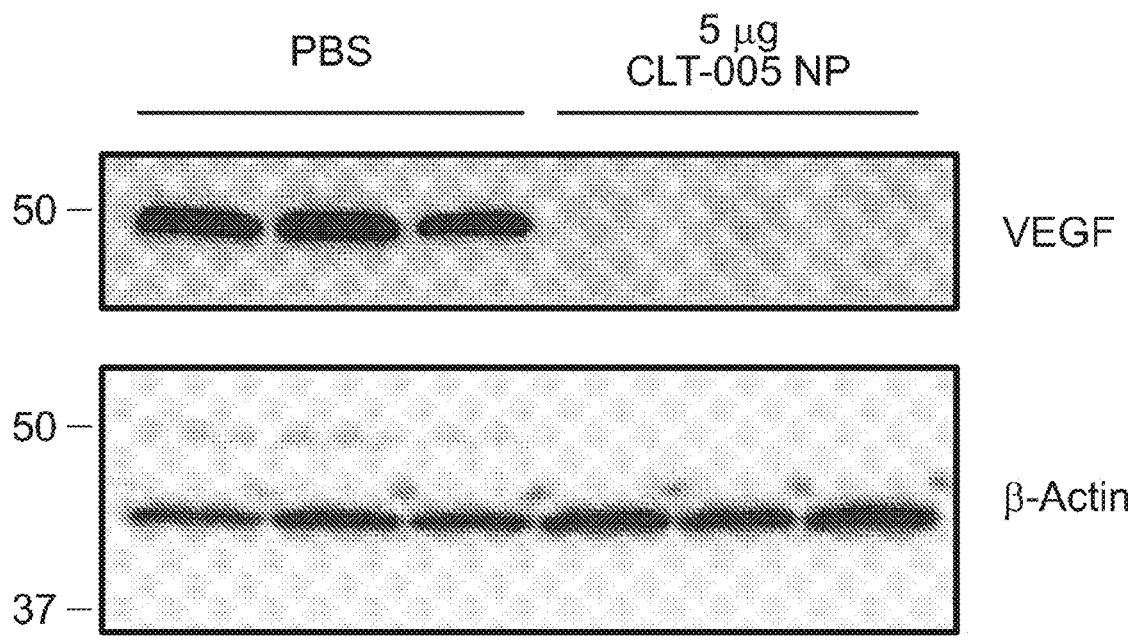
FIG. 17 are immunoblot analysis of embodiments of experimental data demonstrating that CLT-005 reduces retinal VEGF levels in an STZ-diabetes model.

To examine the potency of CLT-005 on reducing protein expression of the pro-angiogenic molecule, VEGF, sustained release nanoparticles (NPs) were prepared to package CLT-005 and performed intravitreal injections in STZ-diabetic rats. For all animals, one eye was injected with 5 μg of CLT-005 NPs and the contralateral eye received PBS as a control. At 14 days post-injection, the retinas were harvested, and immunoblot analyses were performed to visualize VEGF levels (FIG. 17). Intravitreal delivery of CLT-005 NPs nearly abolished protein expression of VEGF, as compared to the contralateral eyes injected with PBS.

According to embodiments of experimental data shown in FIG. 17, two weeks following induction of diabetes with STZ, rats received an intravitreal injection of 5 μg of CLT-005 NPs in one eye and PBS in the contralateral eye. At 14 days post injection The retinal levels of VEGF and β-Actin were then examined with immunoblot analyses. In stark contrast to the contralateral control eye, no VEGF was detectable in the eyes receiving the CLT-005 NPs.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A composition comprising:
a pharmaceutical carrier and an amount, therapeutically effective for the treatment of a retinal disease, of an agent having the formula:

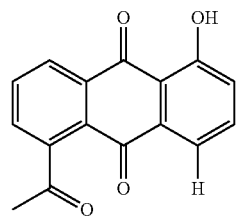

wherein the retinal disease is characterized by at least one of inflammation, angiogenesis, or neovascularization; and
wherein the composition is prepared for administration intravitreally.

2. A method of treating a retinal disease in a subject, comprising:
administering intravitreally to the subject's eye a composition comprising a pharmaceutical carrier and an amount, therapeutically effective for the treatment of the retinal disease, of an agent having the formula:

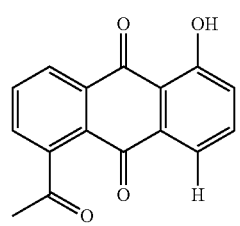

wherein the retinal disease is characterized by at least one of inflammation, angiogenesis, or neovascularization.

3. The method of claim 2, wherein the retinal disease comprises age-related macular degeneration.

4. The method of claim 2, wherein the retinal disease comprises endophthalmitis.

5. The method of claim 2, wherein the retinal disease comprises retinal edema.

6. The method of claim 2, wherein the retinal disease comprises diabetic macular edema.

7. The method of claim 2, wherein the retinal disease comprises diabetic retinopathy.

8. The method of claim 2, wherein the retinal disease is characterized by inflammation.

9. The method of claim 2, wherein the retinal disease is characterized by angiogenesis.

10. The method of claim 2, wherein the retinal disease is characterized by neovascularization.

* * * * *